US008568799B2

(12) United States Patent
Jia et al.

(10) Patent No.: US 8,568,799 B2
(45) Date of Patent: *Oct. 29, 2013

(54) ISOLATION OF A DUAL COX-2 AND 5-LIPOXYGENASE INHIBITOR FROM ACACIA

(75) Inventors: Qi Jia, Superior, CO (US); Timothy C. Nichols, San Diego, CA (US); Eric E. Rhoden, Duluth, GA (US); Scott Waite, Torrance, CA (US)

(73) Assignee: Unigen, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/355,362

(22) Filed: Jan. 20, 2012

(65) Prior Publication Data

US 2012/0329863 A1 Dec. 27, 2012

Related U.S. Application Data

(63) Continuation of application No. 11/457,388, filed on Jul. 13, 2006, now Pat. No. 8,124,134, which is a continuation of application No. 10/104,477, filed on Mar. 22, 2002, now Pat. No. 7,108,868.

(51) Int. Cl.
*A01N 65/00* (2009.01)
(52) U.S. Cl.
USPC .......................................................... 424/725
(58) Field of Classification Search
None
See application file for complete search history.

(56) References Cited

U.S. PATENT DOCUMENTS

| | | | |
|---|---|---|---|
| 3,686,872 A | 8/1972 | Whitworth et al. |
| 3,706,581 A | 12/1972 | Whitworth et al. |
| 4,035,510 A | 7/1977 | Van Scott et al. |
| 4,201,776 A | 5/1980 | Naito et al. |
| 4,268,517 A | 5/1981 | Niebes et al. |
| 4,374,824 A | 2/1983 | Wahmi |
| 4,515,804 A | 5/1985 | Marti et al. |
| 4,627,977 A | 12/1986 | Gaffar et al. |
| 4,946,684 A | 8/1990 | Blank et al. |
| 4,965,067 A | 10/1990 | Wietfeldt |
| 5,096,701 A | 3/1992 | White, Jr. et al. |
| 5,098,709 A | 3/1992 | Kang |
| 5,156,835 A | 10/1992 | Nabi et al. |
| 5,437,856 A | 8/1995 | Lukacovic et al. |
| 5,443,983 A | 8/1995 | Ochoa et al. |
| 5,470,589 A | 11/1995 | Shi |
| 5,545,411 A | 8/1996 | Chancellor |
| 5,585,371 A | 12/1996 | Lardy |
| 5,589,160 A | 12/1996 | Rice |
| 5,605,929 A | 2/1997 | Liao et al. |
| 5,643,598 A | 7/1997 | Meybeck |
| 5,650,432 A | 7/1997 | Walker et al. |
| 5,650,433 A | 7/1997 | Watanabe et al. |
| 5,651,987 A | 7/1997 | Fuisz |
| 5,756,538 A | 5/1998 | Cassels et al. |
| 5,766,614 A | 6/1998 | Yong |
| 5,773,014 A | 6/1998 | Perrier et al. |
| 5,795,911 A | 8/1998 | Cheng et al. |
| 5,804,168 A | 9/1998 | Murad |
| 5,852,057 A | 12/1998 | Muto et al. |
| 5,858,371 A | 1/1999 | Singh et al. |
| 5,886,029 A | 3/1999 | Dhaliwal |
| 5,886,155 A | 3/1999 | Armah et al. |
| 5,908,628 A | 6/1999 | Hou |
| 5,922,756 A | 7/1999 | Chan |
| 5,962,517 A | 10/1999 | Murad |
| 5,968,973 A | 10/1999 | Cheng et al. |
| 6,080,401 A | 6/2000 | Reddy et al. |
| 6,083,921 A | 7/2000 | Xu |
| 6,093,403 A | 7/2000 | Huo et al. |
| 6,113,909 A | 9/2000 | Han et al. |
| 6,126,940 A | 10/2000 | Takahashi et al. |
| 6,126,950 A | 10/2000 | Bindra et al. |
| 6,193,977 B1 | 2/2001 | Han et al. |
| 6,194,469 B1 | 2/2001 | Nair et al. |
| 6,197,808 B1 | 3/2001 | Cheng et al. |
| 6,217,875 B1 | 4/2001 | Murai et al. |
| 6,221,341 B1 | 4/2001 | Montgomery |
| 6,235,294 B1 | 5/2001 | Perrier et al. |
| 6,241,972 B1 | 6/2001 | Herms et al. |
| 6,248,341 B1 | 6/2001 | Anderson et al. |
| 6,264,926 B1 | 7/2001 | Farooqi et al. |
| 6,264,995 B1 | 7/2001 | Newmark et al. |
| 6,280,751 B1 | 8/2001 | Fletcher et al. |
| 6,290,995 B1 | 9/2001 | Xinxian |
| 6,319,523 B1 | 11/2001 | Zhou |

(Continued)

FOREIGN PATENT DOCUMENTS

| | | |
|---|---|---|
| CA | 2 126 513 A1 | 1/1995 |
| CA | 2 451 844 A1 | 1/2003 |

(Continued)

OTHER PUBLICATIONS

*Indian Herbal Pharmacopoeia* (Revised New Edition 2002). Indian Drug Manufacturers' Association, Mumbai, India, 2002, pp. 1-11.
Kang et al., "Antithrombotic Activities of Green Tea Catechins and (−)-Epigallocatechin Gallate," *Thrombosis Research* 96(3):229-237, Nov. 1, 1999. (Abstract only).
Levy et al., "Safety and efficacy of flavonoid compared with naproxen osteoarthritis of the knee: a pilot study," *ICRS 2007*, 5 pages.
Nakagami et al., "Anti-complementary substance used as therapeutic agent—comprises gallic acid, methyl gallate, acetyl-salicylic acid, caffeic acid, catechin, epi-gallo-catechin gallate, myriceten, quercitrin and/or baicalein, or their salts," WPI Accession No. 1995-325471 Derwent Abstract XP002418722, & JP 07 223941 A, Aug. 22, 1995, 1 page.

(Continued)

Primary Examiner — Michael Meller
(74) Attorney, Agent, or Firm — Seed IP Law Group PLLC

(57) ABSTRACT

The present disclosure provides compositions and methods for alleviating inflammatory-associated diseases and conditions. These methods include administering individual and/or a mixture of multiple flavans isolated from a single or multiple *Acacia* genus of plants. The present disclosure also includes methods for isolating and purifying from an *Acacia* genus of plants a composition of flavans having dual specificity for cyclooxygenase (COX-2) and 5-lipoxygenase (5-LO) enzymes.

18 Claims, 14 Drawing Sheets

(56) References Cited

U.S. PATENT DOCUMENTS

| | | |
|---|---|---|
| 6,333,304 B1 | 12/2001 | Bath et al. |
| 6,387,416 B1 | 5/2002 | Newmark et al. |
| 6,391,346 B1 | 5/2002 | Newmark et al. |
| 6,391,872 B1 | 5/2002 | Marfat |
| 6,475,530 B1 | 11/2002 | Kuhrts |
| 6,555,573 B2 | 4/2003 | Rosenbloom |
| 6,576,660 B1 | 6/2003 | Liao et al. |
| 6,685,971 B2 | 2/2004 | Xu |
| 7,045,158 B2 | 5/2006 | Wolfson et al. |
| 7,074,438 B2 | 7/2006 | Xu |
| 7,108,868 B2 | 9/2006 | Jia et al. |
| 7,189,385 B2 | 3/2007 | Montgomery |
| 7,192,611 B2 | 3/2007 | Jia et al. |
| 7,225,870 B2 | 6/2007 | Pedersen et al. |
| 7,514,469 B2 | 4/2009 | Jia |
| 7,531,521 B2 | 5/2009 | Burnett et al. |
| 7,615,239 B2 | 11/2009 | Santo et al. |
| 7,674,830 B2 | 3/2010 | Jia |
| 7,695,743 B2 | 4/2010 | Jia et al. |
| 7,897,182 B2 | 3/2011 | Woo et al. |
| 7,972,632 B2 | 7/2011 | Jia |
| 8,034,387 B2 | 10/2011 | Jia et al. |
| 8,124,134 B2 | 2/2012 | Jia et al. |
| 8,148,416 B2 | 4/2012 | El-Naggar et al. |
| 2001/0002407 A1 | 5/2001 | Nair et al. |
| 2001/0026813 A1 | 10/2001 | Kim et al. |
| 2001/0046963 A1 | 11/2001 | Wenzel et al. |
| 2002/0086070 A1 | 7/2002 | Kuhrts |
| 2002/0122836 A1 | 9/2002 | Obukowicz et al. |
| 2002/0136784 A1 | 9/2002 | Obukowicz et al. |
| 2002/0146467 A1 | 10/2002 | Jung et al. |
| 2003/0013463 A1 | 1/2003 | Yen |
| 2003/0045562 A1 | 3/2003 | EL-Naggar et al. |
| 2003/0102030 A1 | 6/2003 | Reichert et al. |
| 2003/0105030 A1 | 6/2003 | Liao et al. |
| 2003/0125264 A1 | 7/2003 | Malik |
| 2003/0165588 A1 | 9/2003 | Jia et al. |
| 2003/0166583 A1 | 9/2003 | Yoa-Pu Hu et al. |
| 2003/0203857 A1 | 10/2003 | Ohnogi et al. |
| 2004/0057908 A1 | 3/2004 | Bowen et al. |
| 2004/0185124 A1 | 9/2004 | Hayashi |
| 2004/0220119 A1 | 11/2004 | Jia |
| 2005/0049206 A1 | 3/2005 | Gong et al. |
| 2005/0096281 A1 | 5/2005 | Jia et al. |
| 2006/0008749 A1 | 1/2006 | Sobel et al. |
| 2006/0079467 A1 | 4/2006 | Jia et al. |
| 2006/0140881 A1 | 6/2006 | Xu et al. |
| 2006/0141073 A1 | 6/2006 | Worrell et al. |
| 2006/0166583 A1 | 7/2006 | O'Regan et al. |
| 2006/0177528 A1 | 8/2006 | Jia |
| 2006/0204596 A1 | 9/2006 | Jia et al. |
| 2007/0065524 A1 | 3/2007 | Wang |
| 2007/0264361 A1 | 11/2007 | Jo et al. |
| 2008/0107759 A1 | 5/2008 | Woo et al. |
| 2008/0176811 A1 | 7/2008 | Geers et al. |
| 2008/0214658 A1 | 9/2008 | Woo et al. |
| 2008/0279969 A1 | 11/2008 | Jo et al. |
| 2009/0304830 A1 | 12/2009 | Jo et al. |
| 2011/0117224 A1 | 5/2011 | Woo et al. |
| 2011/0207806 A1 | 8/2011 | Jia |
| 2011/0245333 A1 | 10/2011 | Jia et al. |
| 2012/0053138 A1 | 3/2012 | Jia et al. |
| 2012/0329863 A1 | 12/2012 | Jia et al. |

FOREIGN PATENT DOCUMENTS

| | | |
|---|---|---|
| CA | 2 484 192 A1 | 11/2003 |
| CN | 1057196 A | 12/1991 |
| CN | 1093914 A | 10/1994 |
| CN | 1096680 A | 12/1994 |
| CN | 1101856 A | 4/1995 |
| CN | 1189365 A | 8/1998 |
| CN | 1043406 C | 5/1999 |
| CN | 1228968 A | 9/1999 |
| CN | 1285202 A | 2/2001 |
| EP | 0 296 625 | 12/1988 |
| EP | 0 633 022 A2 | 1/1995 |
| EP | 0 742 012 A2 | 11/1996 |
| EP | 0 633 022 B1 | 2/1997 |
| EP | 0 956 867 A1 | 11/1999 |
| EP | 1 147 764 A2 | 10/2001 |
| FR | 2 651 132 A1 | 3/1991 |
| FR | 2 687 572 A1 | 8/1993 |
| GB | 2 024 817 A | 1/1980 |
| GB | 2 306 321 A | 5/1997 |
| JP | 57-038721 A | 3/1982 |
| JP | 61-050921 A | 3/1986 |
| JP | 61-083179 A | 4/1986 |
| JP | 61-161219 A | 7/1986 |
| JP | 61-238719 A | 10/1986 |
| JP | 10-182415 A | 7/1989 |
| JP | 3-240725 A | 10/1991 |
| JP | 03-251518 A | 11/1991 |
| JP | 05271088 A | 10/1993 |
| JP | 7-10768 A | 1/1995 |
| JP | 7-25761 A | 1/1995 |
| JP | 7017847 A | 1/1995 |
| JP | 7-055895 B2 | 6/1995 |
| JP | 7-165598 A | 6/1995 |
| JP | 7-223941 A | 8/1995 |
| JP | 7-242555 A | 9/1995 |
| JP | 7-277942 A | 10/1995 |
| JP | 8-026969 A | 1/1996 |
| JP | 8-104268 A | 4/1996 |
| JP | 5-331061 A | 12/1996 |
| JP | 9-227374 A | 9/1997 |
| JP | 10-025238 A | 1/1998 |
| JP | 63-027435 A | 2/1998 |
| JP | 10-130162 A | 5/1998 |
| JP | 10-287528 A | 10/1998 |
| JP | 11-140497 A | 5/1999 |
| JP | 2000-044481 A | 2/2000 |
| JP | 2000-506901 A | 6/2000 |
| JP | 2000-226329 A | 8/2000 |
| JP | 2000-31954 A | 11/2000 |
| JP | 2001-220353 A | 8/2001 |
| JP | 2002-53484 A | 2/2002 |
| JP | 2003-081746 A | 3/2003 |
| JP | 2003-212771 A | 7/2003 |
| JP | 2003-212786 A | 7/2003 |
| JP | 20047-244385 A | 9/2004 |
| KR | 1996-0003725 A | 2/1996 |
| KR | 1996-0040370 A | 12/1996 |
| KR | 2001-0017481 A | 3/2001 |
| KR | 2001-0069130 A | 7/2001 |
| KR | 2002-0013675 A | 2/2002 |
| KR | 2002-0031608 A | 5/2002 |
| KR | 2003-0021640 A | 3/2003 |
| KR | 10-0465113 B1 | 12/2004 |
| KR | 10-0522579 B1 | 10/2005 |
| WO | 97/36497 A2 | 10/1997 |
| WO | 98/19651 A1 | 4/1998 |
| WO | 98/40086 A2 | 9/1998 |
| WO | 98/42363 A1 | 10/1998 |
| WO | 98/49256 A1 | 11/1998 |
| WO | 00/59523 A1 | 10/2000 |
| WO | 00/67749 A1 | 11/2000 |
| WO | 00/74662 A2 | 12/2000 |
| WO | 01/30341 A1 | 5/2001 |
| WO | 02/07745 A1 | 1/2002 |
| WO | 02/09699 A2 | 2/2002 |
| WO | 02/39973 A2 | 5/2002 |
| WO | 02-42429 A2 | 5/2002 |
| WO | 02/47615 A2 | 6/2002 |
| WO | 03/009825 A2 | 2/2003 |
| WO | 03/015766 A1 | 2/2003 |
| WO | 03-024470 A1 | 3/2003 |
| WO | 03/082312 A1 | 10/2003 |
| WO | 03/092599 A2 | 11/2003 |
| WO | WO 2004/075844 A2 | 9/2004 |
| WO | 2004/089392 A1 | 10/2004 |

(56) References Cited

FOREIGN PATENT DOCUMENTS

| | | |
|---|---|---|
| WO | WO 2004/089392 A1 | 10/2004 |
| WO | 2005/020932 A2 | 3/2005 |
| WO | 2006/099217 A2 | 9/2006 |

OTHER PUBLICATIONS

*Römpp Encyclopedia Natural Products*, eds, W. Steglich, B. Fugmann and S. Lang-Fugmann, Georg Thieme Verlag, Stuttgart, Germany, 2000, p. 630, 3 pages.

Shibata et al., "Pharmacological Study of Kumazasa (Report 1) Acute toxicity, anti-inflammatory and antiulcerative effects of kumazasa water soluble fraction (Folin)," Folia pharmacol japon 71(5)481-490, 1975. (English translation provided.), 11 pages.

Xu et al., "[Stduy on flavonoids in *Ligustrum lucidum*]," Zhong Yao Cai 30(5):538-540, May 2007, 1 page. (English Abstract only).

Zhang et al., *China Journal of the Chinese Materia Medical* 27(4):254-257, 2002, (English translation provided.) 5 pages.

Agarwal et al., "Protection Against Ultraviolet B Radiation-Induced Effects in the Skin of SKH-1 Hairless Mice by a Polyphenolic Fraction Isolated From Green Tea," *Photochem. Photobiol.* 58(5): 695-700, Nov. 1993.

Amos et al., "The Pharmacological Effects of an Aqueous Extract from *Acacia nilotica* Seeds," *Phytotherapy Res* 13: 683-685, 1999.

Azad et al, "Isolation of (+)-catechin and a new polyphenolic compound in Bengal catechu," *J Wood Sci* 47(5): 406-409, 2001.

Bastianetto et al., "Neuropeotective abilities of resveratrol and other red wine constituents against nitric oxide-related toxicity in cultured hippocampal neurons," *Br. J. Pharmacol.* 131: 711-720, 2000.

Baumann et al., "Flavonoids and Related Compounds as inhibitors of Arachidonie Acid Peroxidation," *Prostaglandins* 20(4): 627-639, Oct. 1980.

Chang et al., "Role of 5-Lipoxygenase Products of Arachidonic Acid in Cell-to-Cell interaction Between Macrophages and Natural Killer Cells in Rat Spleen," *J Leukocyte Biol* 50:273-278, 1991.

Dafallah et al., "Investigation of the Anti-inflammatory Activity of *Acacia nilotica* and *Hibiscus sabdariffa*," *Amer J Chin Med* 24(3-4):263-269, 1996.

Deshpande et al., "Flavonoids of *Acacia catechu* Heartwood" *Indian J Chem 20B*:628, Jul. 1981.

Exotic Naturals, "*Acacia catechu* Extract," retrieved Apr. 19, 2007 from, www.exoticnatural.com/acacia-catechu.htm, 2 pages.

Gilani et al., "Studies on Antihypertensive and Antispasmodic Activities of Methanol Extract of *Acacia nilotica* Pods," *Phytotherapy Res* 13(8):665-669, Dec. 1999.

Hagos et al., "Isolation of Smooth Muscle Relaxing 1,3-Diarylpropan-2-ol Derivatives from *Acacia tortilis*," *Planta Med* 53(1):27-31, Feb. 1987.

Hamazaki et al., "An effect of inhibiting production of LTC4 by catechin," *Allergy* 49(9/10):914, 2000. (with English translation).

Hanausek-Walaszek et al., Inhibitory Effects of Triterpenoid Saponins From *Acacia victoriae* on Dimethylbenz [A] Anthracene-Induced Murine Skin Cardinogenesis, *Proceedings American Association for Cancer Research Annual Meeting* 41:663 (Abstract #4216), Mar. 2000.

Haridas et al., "Avicins: Novel Triterpenoid Saponins from *Acacia victoriae* (Benth) Induce Apoptosis by Mitochondrial Perturbation," *Proceedings American Association for Cancer Research Annual Meeting* 41:361 (Abstract #3820), Mar. 2000.

Hong et al., "Effects of purified green and black tea polyphenols on cyclooxygenase- and lipoxygenase-dependent matabolism of arachidonic acid in human colon mucosa and colon tumor tissues," *Biochem. Pharmacol.* 62: 1175-1183, 2001.

Hukkeri et al., "Anti-Inflammatory Activity of Leaves of *Acacia farnesiana* Willd," *Indian Drugs* 39(12): 664-666, Dec. 1, 2002.

Kalkbrenner et al., "In vitro Inhibition and Stimulation of Purified Prostaglandin Endoperoxide Synthase by Flavonoids: Structure-Activity Relationship," *Pharmacol* 44(1): 1-12, 1992.

Kim et al., "Pharmacological Activities of Flavonoids (I)—Relationships of Chemical Structure of Flavonoids and their Inhibitory Activity of Hypersensitivities," *Yakhak Hoeji* 34(5): 348-364, 1990.

Laughton, et al., "Inhibition of Mammalian 5-Lipoxygenase and Cyclo-Oxygenase by Flavonoids and Phenolic Dietary Additives," *Biochem Pharmacol* 42(9): 1673-1681, 1991.

Medicine.net, "Rheumatoid Arthritis (RA)," retrieved from www.medicinenet.com/rheumatoid_arthritis/article.htm, Jun. 4, 2009, 4 pages.

Min et al., "(−)-Epiafzelechin: Cyclooxygenase-1 Inhibitor and Anti-inflammatory Agent from Aerial Parts of *Celastrus orbiculatus*," *Planta Med.* 65: 460-462, 1999.

Miyamoto et al., "Studies on selection method of crude drugs by statistical analysis. Research on Rhubarb having anti-inflammatory activity," *Natural Med* 55(4): 159-164, 2001. (with English abstract).

Murari et al., "A Study of the Components of Cutch: Isolation of Catechin, Gallocatechin, Dicatechin & Catechin Tetramer as Methyl Ethers," *Indian J Chem* 14B(9):661-664, 1976.

Murase et al., "Beneficial effects of tea catechins on diet-induced obesity: stimulation of lipid catabolism in the liver," *International Journal of Obesity* 26: 1459-1464, 2002.

Mutoh et al., "Suppression by Flavonoids of Cyclooxygenase-2 Promoter-dependent Transcriptional Activity in Colon Cancer Cells: Structure-Activity Relationship," *Jpn J Cancer Res* 91(7):686-691, Jul. 2000.

Nadkarni, ed., *Dr. K.M. Nadkarni's Indian Materia Medico: With Ayurvedic, Unani-Tibbi, Siddha, Allopathic, Homeopathic, Naturopathic& Home Remedies, Appendicces & Indexes*: vol. 1, Popular Prakashan, London, 1996, pp. 8-17. (8 pages).

Nakagami et al., "Anti-complementary acid, caffeic acid, catechin, epigallocatechin gallate, muricetin, quercitrin, baicalein and their pharmacologically acceptable salts," WPI/Thomson Database, Accession No. 1995-35471 [42], Feb. 14, 1994.

Noreen et al., "Development of a Radiochemical Cyclooxygenase-1 and -2 in Vitro Assay for Identification of Natural Products as Inhibitors of Prostaglandin Biosynthesis," *J Nat Prod* 61:2-7, Jan. 1998.

Noreen et al., "Flavan-3-ols Isolated From Some Medicinal Plants Inhibiting COX-1 and COX-2 Catalysed Prostaglandin Biosynthesis," *Planta Medica* 64:520-524, 1998.

Noreen et al., "Two New Isoflavones from *Ceiba pentandra* and Their Effect on Cyclooxygenase-Catalyzed Prostaglandin Biosynthesis," *J Nat Prod* 61: 8-12, Jan. 1998.

Park et al., "Involvement of ERK and Protein Tyrosine Phosphatase Signaling Pathways in EGCG-Induced Cyclooxygenase-2 Expression in Raw 264.7 Cells," *Biochem Biophys Res Commun* 286:721-725, 2001.

Ramesiiwaii et al., "Chemical Constituents of Acacia," 1997.

Sekine et al., "Structure and Synthesis of a New Monoterpenoidal Carboxamide from the Seeds of the Thai Medicinal Plant *Acacia concinna*," *Chem and Pharm Bull* 45(1):148-151, 1997.

Shah et al., "The Antiplatelet Aggregator Activity of *Acacia nilotica* is Due to Blockade of Calcium Influx through Membrane Calcium Channels," *Gen Pharmac* 29(2):251-255, 1997.

Sharma, "Chemical Constituents of *Acacia catechu* Leaves," *J Indian Chem Soc* 74:60, Jan. 1997.

SmartSkinCare.com, "What green tea can and cannot do for your skin," retrieved Jun. 5, 2009, from www.smartskincare.com/treatments/topical/greentea.html, 3 pages.

Takada, "Catechin-containing soap includes tea-originated catechin as one of green tea ingredients," WPI/Thomson Database, Accession No. 1999-367373 [31], Oct. 31, 1997, 1 page.

Exhibit 4, of Remarks Made in an Amendment, filed Jul. 2, 2008, for U.S. Appl. No. 10/427,746, 2 pages.

Exhibit 11, of Remarks Made in an Amendment, filed Jul. 2, 2008, for U.S. Appl. No. 10/427,746, 3 pages.

Exhibit 9A, of Remarks Made in an Amendment, filed Jul. 2, 2008, for U.S. Appl. No. 10/427,746, 2 pages.

Exhibit 12A and 12B, of Remarks Made in an Amendment, filed Jul. 2, 2008, for U.S. Appl. No. 10/427,746, 2 pages.

Exhibit 14, of Amendment filed Jul. 2, 2008, for U.S. Appl. No. 10/427,746, 5 pages.

Exhibit 15, of Amendment filed Jul. 2, 2008, for U.S. Appl. No. 10/427,746, 25 pages.

Exhibit 16, of Remarks Made in an Amendment, filed Jul. 2, 2008, for U.S. Appl. No. 10/427,746, 8 pages.

(56) References Cited

OTHER PUBLICATIONS

"L17—(baicalin near20 catechin) near20 weight" Search History, retrieved Jan. 8, 2009, from http://jupiter1:42900/bin/cgi-bin/PreSearch.p1, 1 page.

"Scutellaria Root/*Official Monographs for Part II*," in The Japanese Pharmacopoeia, 14th ed. (English version), Society of Japanese Pharmacopoeia, Tokyo, Japan, 2001, pp. 1042-1043. (4 pages).

Abdulrazak et al., "Chemical Composition, Phenolic Concentration and In Vitro Gas Production Characteristics of Selected Acacia Fruits and Leaves," *Asian-Aus J Anim Sci* 13(7):935-940, 2000.

Afolayan et al., "The antimicrobial activity of 3,5,7-trihydroxyflavone isolated from the shoots of *Helichrysum aureonitens*," *J Ethnopharm* 57(3):177-181, 1997.

Ali Ibn-e-Abbaas Majoosi; Kaamil-al-Sena'ah, Part II (10$^{th}$ century AD), Central Council for Research in Unani Medicine, 61-65 Institutional Area, Janak Puri, New Delhi-58, 2005 AD p. 129, Formulation ID: AH3/876C, Formulation Name: Zimaad Baraae Qooba, 3 pages. (with English translation).

Ardlie et al., "Effects of Trifluoperazine on Platelet Activation," *Thromb Res* 38(6):695-706, 1985.

Arnaud, "COX-2: an in vivo evidence of its participation in heat stress-induced myocardial preconditioning," *Cardiovas Res* 58:582-588, 2003.

Asaki et al., "The Effect of Oral Rinses Extracted from Japanese Tea on the Experimental Gingivitis in Man," *J Jap Assoc Peridontol* 37(2):412-421, 1995. (Abstract only).

Babu et al., "Aspirin and Asthma," *Chest* 118:1470-1476, 2000.

Bertolini et al., "Dual Acting Anti-Inflammatory Drugs: A Reappraisal," *Pharmacol Res* 44(6):437-450, 2001.

Bhagwat et al., "Flavanoid composition of tea: Comparison of black and green teas," 2003 IFT Annual Meeting and Food Expo, Jul. 12-16, 2003, Chicago, Illinois, 1 page (Poster).

Bhāvamiśra; Bhāvaprakāśa—Edited & translated by Brahmashankara Misra & RupaLalaji Vaisya, Part-I: Chaukhambha Sanskrit Sansthan, Varanasi, Edn. 9$^{th}$, 1999, Time of origin 16$^{th}$ century, p. 110, Formulation ID: RS/3007D, Formulation Name: Dantakūrcikā(04), 3 pages. (with English translation).

Bickford et al., "Effect of Normobiaric Hyperoxia on Two indexes of Synaptic Function in Fisher 344 Rats," *Free Rad Biol Med* 26(7/8):817-824, Apr. 1999.

Bickford et al., "Effects of aging on cerebellar noradrenergic function and motor learning: nutritional interventions," *Mech Ageing Dev* 111:141-154, Nov. 1999.

Bickford et al., "Antioxidant-rich diets improve cerebellar physiology and motor learning in aged rats," *Brain Res* 866:211-217, Jun. 2, 2000.

Boozer et al., "An herbal supplement containing Ma Huang-Guarana for weightloss: a randomized, double-blind trial," *International Journal of Obesity* 25: 316-324, 2001.

Bosset et al., "Photoageing shows histological features of chronic skin inflammation without clinical and molecular abnormalities," *Brit J Dermatol* 149:826-835, 2003.

Boumendjel et al., "B-ring Substituted 5,7-Dihydroxyflavonols with High-Affinity Binding to P-Glycoprotein Responsible for Cell Multidrug Resistance," *Bioorg Med Chem Lett* 11(1):75-77, Jan. 8, 2001.

Brideau et al., "A human whole blood assay for clinical evaluation of biochemical efficacy of cyclooxygenase inhibitors," *Inflamm Res* 45:68-74, 1996.

Brock et al., "Arachidonic Acid is Preferentially Metabolized by Cyclooxygenase-2 to Prostacyclin and Prostaglandin $E_2$," *J Biol Chem* 274(1): 11660-11666, Apr. 1999.

Bunting et al., "The Prostacyclin-Thromboxane $A_2$ Balance: Pathophysiotogical and Therapeutic Implications," *Br Med Bull* 39(3):271-276, 1983.

Butenko et al., "Anti-inflammatory properties and inhibition of leukotriene $C_4$ biosynthesis in vitro by flavonoid baicalein from *Scutellaria baicalensis* georgy roots," *Agents Actions Special Conference Issue* 39:C49-C51, 1993.

Butterfield et al., "Structural and Functional Changes in Proteins Induced by Free Radical-mediated Oxidative Stress and Protective Action of the Antioxidants N-tert-Butyl-α-phenylnitrone and Vitamin $E^d$," *Ann NY Acad Sci* 854:448-462, Nov. 20, 1998.

Cao et al., "Hyperoxia-induced changes in antioxidant capacity and the effect of dietary antioxidants," *J Applied Physiol* 86(6):1817-1822, Jun. 1999.

Cao et al., "Oxygen-Radical Absorbance Capacity Assay for Antioxidants," *Free Radical Biology & Medicine* 14:303-311, 1993.

Carney et al., "Reversal of age-related increase in brain protein oxidation, decrease in enzyme activity, and loss in temporal and spatial memory by chronic administration of the spin-trapping compound N-tert-butyl-α-phenylnitrone," *Proc. Natl. Acad. Sci. USA* 88:3633-3636, May 1991.

Carson et al., "The cellular response in neuroinflammation: The role of leukocytes, microglia and astrocytes in neuronal death and survival," *Clin Neurosci Res* 6(5):237-245, Dec. 2006.

Cartford et al., "Eighteenth-Month-Old Fischer 344 Rats Fed a Spinach-Enriched Diet Show Improved Delay Classical Eyeblink Conditioning and Reduced Expression of Tumor Necrosis Factor α (TNFα) and TNFβ in the Cerebellum," *J Neurosci* 22(14):5813-5816, Jul. 15, 2002.

Caughey et al., "Roles of Cyclooxygenase (COX)-1 and COX-2 in Prostanoid Production by Human Endothelial Cells: Selective Up-Regulation of Prostacyclin Synthesis by COX-2," *J Immunol* 167:2831-2837, 2001.

Celotti et al., "Anti-inflammatory Drugs: New Muititarget Compounds to Face an Old Problem. The Dual Inhibition Concept," *Pharmacological Research* 43(5):429-436, May 2001.

Chang et al., "Prevention of Lens Protein-induced Ocular Inflammation with Cyclooxygenase and Lipoxygenase Inhibitors," *J Ocular Pharmacol* 5(4):353-360, 1989.

Chen et al., "Wogonin, baicalin, and baicalein inhibition of inducible nitric oxide synthase and cyclooxygenase-2 gene expressions induced by nitric oxide synthase inhibitors and lipopolysaccharide," *Biochem Pharmacol* 61(11):1417-1427, Jun. 1, 2001.

Chen et al., "Oroxylin A inhibition of Lipopolysaccharide-Induced iNOS and COX-2 Gene Expression via Suppression of Nuclear factor-κB activation," *Biochem Pharmacol* 59(11):1445-1457, Jun. 1, 2000.

Chi et al., "Effect of wogonin, a plant flavone from Scutellaria radix, on the suppression of eyelooxygenase-2 and the induction of inducible nitric oxide synthase in lipopolysaccharide-treated RAW 264.7 cells," *Biochem Pharmacol* 61:1195-1203, May 15, 2001.

Chinese Herbs Direct, retrieved from http://www.chineseherbsdirect.com, 2007, 2 pages.

Chou et al., "The Antiinflammatory and Analgesic Effects of Baiclin in Carrageenan-Evoked Thermal Hyperalgesia," *Anesth Analg* 97:1724-1729, 2003.

Christie et al., "Opiouis, NSAIDs and 5-lipoxygenase inhibitors act synergistically in brain via arachidonic acid metabolism," *Inflamm Res* 48:1-4, 1999.

Chung et al., "Pharmacological Effects of Methanolic Extract from the Root of *Scutellaria baicalensis* and its Flavonoids on Human Gingival Fibroblast," *Planta Medica* 61(2):150-153, Apr. 1995.

Clark et al., "Do Some inhibitors of COX-2 increase the Risk of Thromboembolic Events?," *Drug Safety* 27(7):427-456, 2004.

Commenges et al., "Intake of flavonoids and risk of dementia," *Eur J Epidemiol* 16:357-363, Apr. 2000.

Dannhardt et al., "Cyclooxygenase inhibitors—current status and future prospects," *Eur J Med Chem* 36(2):109-126, Feb. 2001.

Davies et al., "COX-2 selective inhibitors cardiac toxicity: getting to the heart of the matter," *J Pharm Pharmaceut Sci* 7(3):332-336, 2004.

de Gaetano et al., "Prevention of thrombosis and vascular inflammation: benefits and limitations of selective or combined COX-1, COX-2 and 5-LOX inhibitors," *TRENDS in Pharmacol Sci* 24(5):245-252, May 2003.

de la Puerta et al., "Inhibition of Leukocyte Eicosanoid Generation and Radical Scavenging Activity by Gnaphalin, a Lipophilic Flavonol Isolated from *Helichrysum picardii*," *Planta Medico* 65(6):507-511, Aug. 1999.

(56) References Cited

OTHER PUBLICATIONS de Whalley et al., "Flavonoids Inhibit the Oxidative Modification of Low Density Lipoproteins by Macrophages," *Biochem Pharmacol* 39(11):1743-1750, Jun. 1, 1990.
Declaration of Paul H. Caldron, dated Jun. 17, 2008, for U.S. Appl. No. 10/427,746, 4 pages.
Declaration of Edward Cannon, dated Jul. 24, 2008, for U.S. Appl. No. 10/427,746, 4 pages.
Declaration of Matthew D. Heller, dated Jun. 27, 2008, for U.S. Appl. No. 10/427,746, 5 pages.
Declaration of Qi Jia, dated Nov. 6. 2006, for U.S. Appl. No. 10/427,746, 10 pages.
Declaration of Qi Jia, dated Dec. 20, 2004, for U.S. Appl. No. 10/104,477, 5 pages.
DeLange et al., "Phycoerythrin Fluorescence-Based Assay for Peroxy Radicals: A Screen for Biologically Relevant Protective Agents," *Analyt Biochem* 177:300-306, 1989.
Dempke et al., "Cyclooxygenase-2: a novel target for cancer chemotherapy?," *J Cancer Res Clin Oncol* 127(7):411-417, Jul. 2001.
Deray, "Renal and cardiovascular effects of non-steroidal anti-inflammatories and selective cox 2 inhibitors," *Presse Med* 33(7):483-489, Apr. 2004. (with English abstract).
DeWitt, "Cox-2-Selective Inhibitors: The New Super Aspirins," *Mol Pharmacol* 55:625-631, 1999.
Elattar et al., "Hydroxy fatty acids and prostaglandin formation in diseased human periodontal pocket tissue," *J Peridontal Res* 21:169-176, 1986.
Engler et al., "The vasculoprotective effects of fiavonoid-rich cocoa and chocolate," *Nutrition Res* 24:695-706, 2004.
Felson, "Osteoarthritis of the Knee," *N Engl J Med* 354(8):841-848, Feb. 23, 2006.
Fenton et al., "Characterization of the Effects of Antiangiogenic Agents on Tumor Pathophysiology," *Am J Clin Oncol (CCT)* 24(5):453-457, 2001.
Fioruuci et al., "Dual Inhibitors of cyclooxygenase and 5-lipoxygenase. A new avenue in anti-inflammatory therapy?," *Biochem Pharmacol* 62:1433-1438, 2001.
Fogh et al., "Modulation of Licosanoid Formation by Lesional Skin of Psoriasis: An Ex vivo Skin Model," *Acta Derm Venerol (Stockh)* 73:191-193, 1993.
Fosslien, "Review: Cardiovascular Complications of Non-Steroidal Anti-Inflammatory Drugs," *Annals Clin Lab Sci* 35:(4):347-385, 2005.
Friedman et al., "NSAIDs in Dermatologic Therapy: Review and Preview," *J Cutan Med Surg* 6(5):449-459, 2002.
Gabrielska et al., "Antioxidant Activity of Flavones from *scutellaria baicalensis* in Lecithin Liposomes," *Verlag der Zeitschrift für Naturforschung* 52c(11-12): 817-823, 1997.
Gaffar et al., "The effect of triclosan on mediators of gingival inflammation,"*J Clin Peridontal* 22:480-484, 1995.
Gafner et al., "Evaluation of the anti-inflammatory properties of skullcap (*Scutellaria lateriflora* L.) extracts in different in vitro models," 2004 International Congress on Natural Products Research, Phoenix, Arizona, Jul. 31-Aug. 4, 2004, p. 60 and poster. (3 pages).
Gemma et al., "Diets Enriched in Foods with High Antioxidant Activity Reverse Age-Induced Decreases in Cerebellar β-Adrenergic Function and Increases in Proinflammatory Cytokines," *J Neurosci* 22(4):6114-6120, Jul. 15, 2002.
Genco et al., in *Contemporary Periodontics*, The C.V. Mosby Company, St. Louis, pp. 361-370, 1990.
Gilroy et al., "Inducible cyclooxygenase may have anti-inflammatory properties," *Nature Med* 5(6):698-701, Jun. 1999.
Giovannucci et al., "Aspirin and the Risk of Colorectal Cancer in Women," *N Engl J Med* 333(10):609-614, Sep. 7, 1995.
Goebel et al., "Procainamide, a Drug Causing Lupus, Induces Prostaglandin H Synthase-2 and Formation of T Cell-Sensitizing Drug Metabolites in Mouse Macrophages," *Chem Res Toxicol* 12(6):488-500, 1999.

Gök et al., "Role of Leukotrienes on Coronary Vasoconstriction in Isolated Hearts of Arthritic Rats: Effect of in vivo Treatment with CI-986, a Dual Inhibitor of Cyclooxygenase and Lipoxygenase," *Pharmacol* 60:41-46, 2000.
Gould et al., "Antioxidant protection of cerebellar β-adrenergic receptor function in aged F344 rats," *Neurosci Lett* 250:165-168, Jul. 10, 1998.
Greenspan et al., "Carboxy-Substituted Cinnamides: A Novel Series of Potent, Orally Active $LTB_4$ Receptor Antagonists," *J Med Chem* 42(1):164-172, 1999.
Gupta, V.K., Senior Advisor and Director, TKDL, Third Party Observations dated Oct. 9, 2010, in Canadian Application No. 02584125, 7 pages.
Gupta, "Formulation of Dual Cyclooxygenase (COX) and Lipoxygenase (LOX) Inhibitors for Mammal Skin Care," Third Party Observation dated Jul. 2, 2011, for Canadian Application No. 2,521,429, 8 pages.
Gupta, "Flavonoids Composition for treating Oral Disease," Third Party Observation dated May 30, 2011, for European Application No. 05810437.3, 7 pages.
Harrington et al., "Antithrombotic Therapy for Coronary Artery Disease: The Seventh ACCP Conference on Antithrombotic and Thrombolytic Therapy," *Chest* 126 (3 Suppl): 513S-548S, Sep. 2004.
Hase et al., "Histological increase in inflammatory infiltrate in sun-exposed skin of female subjects: the possible involvement of matrix metalloproteinase-1 produced by inflammatory infiltrate on collagen degradation," *Br J Dermatol* 142(2):267-273, 2000.
Hase et al., "Peroxisome proliferator activated receptor (PPAR) dependent gene transcription activators," WPI/Thomson, Accession No. 2002-388616 [44] Mar. 19, 2002, 1 page.
Hennekens, "Update on Aspirin in the Treatment and Prevention of Cardiovascular Disease," *Am J Manag Care* 8(22 Suppl):S691-S700, Dec. 2002.
Heo et al., "Anti-genotoxicity of galangin as a cancer chemopreventive agent candidate," *Mutat Res* 488(2):135-150, May 2001.
Heo et al., "Potent Inhibitory Effect of Flavonoids in *Scutellaria baicalensis* on Amyloid β Protein-Induced Neurotoxicity," *J Agric Food Chem* 52(13):4128-4132, Jun. 30, 2004. (Abstract only).
Herschman, "Regulation of prostaglandin synthase-1 and prostaglandin synthase-2," *Cancer Metastasis Rev* 13(3-4):241-256, Dec. 1994.
Hiipakka et al., "Stucture-activity relationships for inhibition human 5α-reductases by polyphenols," *Biochem Pharmacol* 63:1165-1176, 2002.
Hiraoka, "Long-Term Efficacy of COX-2 Selective Inhibitor Etadolac (Hypen®) on Chronic Low Back Pain and/or Osteoarthritis," *Clin Med* 16(7):1037(107)-1045(115), Jul. 2000. (18 pages).
Imamura et al., "Inhibitory Effects of Flavonoids on Rabbit Heart Carbonyl Reductase," *J Biochem* 127(4):653-658, Apr. 2000.
International Preliminary Examination Report dated Oct. 14, 2005, for International Application No. PCT/US04/010279, 1 page.
International Search Report and Written Opinion issued Sep. 10, 2004, for International Application No. PCT/US04/010279, 5 pages.
International Search Report mailed Dec. 23, 2003, for International Application No. PCT/US03/13463, 4 pages.
Itoigawa et al., "Structure-activity relationship of cardiotonic fliavonoids in guinea-pig papillary muscle," *J Ethnopharmacol* 65(3):267-272, Jun. 1999.
Itou et al., "Compsns. Acting on dental caries and periodontosis—contain polyphenol cpds. pref. obtd. from tea by extn. with water," WPI/Thomson Database, Accession No. 1989-147372 [20] 1989, 1 page.
Jaeckel et al., "Correlation of Expression of Cyclooxygenase-2, Vascular Endothelial Growth Factor, and Peroxisome Proliferator-Activated Receptor δ With Head and Neck Squamous Cell Carcinoma," *Arch Otolaryngol Head Neck Surg* 127(10):1253-1259, Oct. 2001.
Jia et al., "Identification of free-B-ring flavonoids as potent cyclooxygenase 2 (COX-2) inhibitors," Derwent Abstract of U.S. Patent Application No. 2003-165588 A1, Accession No. 139:191432 CA, 1 page.
Jüni et al., "Risk of cardiovascular events and rofecoxib: cumulative meta-analysis," *Lancet.* 364:2021-2029, Dec. 2004.

(56) References Cited

OTHER PUBLICATIONS

Kakegawa et al., "Inhibitory Effects of Tannins on Hyaluronidase Activation and on the Degranulation from Rat Mesentery Mast Cells," *Chem. Pharm, Bull.* 33(11): 5079-5082, 1985.
Kaneko et al., "Protective Effect of Flavonoids on Endothelial Cells against Linoleic Acid Hydroperoxide-induced Toxicity," *Biosci Biotechnol Biochem* 63(2):323-328, 1999.
Kao et al., "Modulation of Endocrine Systems and Food Intake by Green Tea Epigallocatechin Gallate," *Endocrinol* 141(3):980-987, 2000.
Kawasaki et al., "In Vitro Antiallergic Activity of Flavonoids in Histamine Release Assay Using Rat Basophilic Leukemia (RBL-2H3) Cells," *J Food Hyg Soc Japan* 33(5): 497-503, Oct. 1994.
Khanna et al., "Natural products as a gold mine for arthritis treatment," *Current Opinion in Pharmacol* 7:344-351, 2007.
Kikukawa et al., "Mechanisms of suppressive action of TJI14 upon murine type II collagen-induced arthritis," *Ensho* 15(2):129-133, 1995. (Abstract only).
Kimura et al., "Effects of Baicalein Isolated from *Scutellaria baicalensis* Radix on Adhesion Molecule Expression Induced by Thrombin and Thrombin Receptor Agonist Peptide in Cultured Human Umbilical Vein Endothelial Cells," *Planta Medica* 67:331-334, Jun. 2001.
Kirchner et al., "Effects of tepoxalin, a dual inhibitor of cyclooxygenase/5-lipoxygenase, on events associated with NSAID-induced gastrointestinal inflammation," *Prostaglandins, Leukotrienes and Essential Fatty Acids* 56(6):417-423, Jun. 1997.
Kirschenbaum et al., "The role of Cyclooxygenase-2 in Prostate Cancer," *Urology* 58(Suppl 2A):127-131, Aug. 2001.
Klickstein et al., "Lipoxygenation of Arachidonic Acid as a Source of Polymorphonuclear Leukocyte Chemotactic Factors in Synovial Fluid and Tissue in Rheumatoid Arthritis and Spondyloarthritis," *J Clin Invest* 66(5):1166-1170, Nov. 1980.
Koga et al., "Effect of plasma metabolites of (+)-catechin and quercetin on monocyte adhesion to human aortic andothelial cells," *Am J Clin Nutr* 73:941-948, 2001.
Kong, "Aspirin in Cardiovascular Disorders—What is Optimum Dose," *Am J Cardiovasc Drugs* 4(3):151-158, 2004.
Krakauer et al., "The flavonoid baicalin inhibits superantigen-induced inflammatory cytokines and chemokines," *FEBS Lett* 500:52-55, Jun. 29, 2001.
Kubo et al., "Flavonols from *Heterotheca inuloides*: Tyrosinase Inhibitory Activity and Structural Criteria," *Bioorg Med Chem* 8(7):1749-1755, Jul. 2000.
Kubo et al., "Studies on Scutellariae Radix, Part II: The Antibacterial Substance," *J Medicinal Plant Res* 43:194-201, 1981.
Kubo et al., "Studies on Scutellariae radix. VII. Anti-arthritic and Anti-inflammatory Actions of Methanolic Extract and Flavonoid Components from Scuttellariae Radix," *Chem & Pharmaceutical Bulletin* 32(7):2724-2729, Jul. 1984.
Kuhn et al., "Action of cyclooxygenase (COX) and lipoxygenase (LOX) inhibitors as well as of oxygen free radical scavengers (OFRS) in the inflammation-induced vasodepression," *Biomed Biochim Acta* 47(10/11):S320-S323, 1988.
Kulkarni et al.. "Licofelone—A Novel analgesic and Anti-Inflammatory Agent," *Current Topics Med Chem* 7(3):251-263, 2007.
Kuppusamy et al., "Effects of Flavonoids on Cyclic Amp Phosphodiesterase and Lipid Mobilization in Rat Adipocytes," *Biochem Pharmacol* 44(7):1307-1315, 1992.
Kuppusamy et al., "Potentiation of β-Adrenoceptor Agonist-Mediated Lipolysis by Quercetin and Fisetin in Isolated Rat Adipocytes," *Biochem Pharmacol* 47(3):521-529, 1994.
Lamarque, "Safety of the selective inhibitors the inducible cyclooxygenase-2 taken for long period," *Bull Cancer* 91:S117-S124, 2004.
Lee et al., "Inhibition of oxidative DNA damage, 8-OHdG, and carbonyl contents in smokers treated with antioxidants (vitamin E, vitamin C, β-carotene and red ginseng)," *Cancer Lett* 132:219-227, 1998.

Lee et al., "Pharmacokinetics of Tea Catechins after Ingestion of Green Tea and (—)-Epigallocatechin-3-gallate by Humans: Formation of Different Metabolites and Individual Variability," *Cancer Epidemiol Biomarkers & Prev* 11:1025-1032, Oct. 2002.
Lee et al., "Salicylic Acid Peels for the Treatment of Acne Vulgaris in Asian Patients," *Dermatol Surg* 29(12):1196-1199, 2003.
Lenton et al., "Ability of human plasma to protect against ionising radiation is inversely correlated with age" *Mech Ageing Dev* 107:15-20, Feb. 1, 1999.
Leyden, "Guest Editorial," *J Am Acad Dermatol* 49(3 Suppl.):S199, 2003.
Leyden, "A review of the use of combination therapies for the treatment of acne vulgaris," *J Am Acad Dermatol* 49(3 Suppl):S200-S210, 2003. (Abstract only).
Li et al., "Chemoprevention of 7,12-dimethylbenz[a]anthracene (DMBA)-induced oral carcinogenesis in hamster cheek pouch by a cyclooxygenase 2 inhibitor (Celecoxib) and a 5-lipoxygenase inhibitor (Zileuton)," *AACR Meeting Abstracts*, Abstract No. 546-a, 2004. (1 page).
Li, "The effect of Radix Scutellaria on *Porphyromonas endodantalis* in vitro," *West China Journal of Stomatology* 22(1):57-61, 2004. (Abstract Only).
Li et al., "The flavonoid baicalin exhibits anti-inflammatory activity by binding to chemokines," *Immunopharmacol* 49:295-306, Sep. 2000.
Liang et al., "Suppression of inducible cyclooxygenase and nitric oxide synthase through activation of peroxisome proliferator-activated receptor-γ by flavonoids in mouse macrophages," *FEBS Letters* 496(1):12-18, May 4, 2001.
Liao et al., "Selective Inhibition of Steroid 5α-Reductase Isozymes by Tea Epicatechin-3-Gallate and Epigallaocatechin-3-Gallate," *Biochem Biophys Res Comm* 214(3):833-838, 1995.
Lotioncrafter.com, "PEG-7 Glyceryl Cocoate," retrieved Apr. 17, 2008, from http://www.lotioncrafter.com/store/PEG-7-GlycertI-Cocoate-pr-16444.html, 1 page.
Lubrizol, Material Safety Data Sheet: CARBOPOL* ULTREZ 21 Polymer, effective date Oct. 17, 2007, 8 pages.
Lynch, "Age-Related impairment in Long-Term Potentiation in Hippocampus: A Role for the Cytokine, Interleukin-1β?," *Prog Neurobiol* 56:571-589, Dec. 1998.
Mādhavah; Vmadamādhava;—Marathi translated by Dato vallala Borkar; Yagyeswara Gopal Dixit, Bookseller, Pune; Edn. 1922 [Time of origin 9th century], p. 503, Formulation ID: AB/1051, Formulation Name: Khadirodakam, 3 pagfes. (with English translation).
Matsumoto et al., "Concordant Induction of Prostaglandin $E_2$ Synthase with Cyclooxygenase-2 Leads to Preferred Production of Prostaglandin $E_2$ over Thromboxane and Prostaglandin $D_2$ in Lipopolysaccharide-Stimulated Rat Peritoneal Macrophages," *Biochem Biophys Res Commun* 230(1):110-114, 1997.
Mayo Clinic, "Alzheimer's disease," Feb. 10, 2009, 2 pages.
McAdam et al., "Systemic biosynthesis of prostacyclin by cyclooxygenase (COX)-2: The human pharmacology of a selective inhibitor of COX-2," *Proc. Natl. Acad. Sci. USA* 96:272-277, Jan. 1999.
Meyer et al., "Antiviral activity of galangin isolated from the aerial parts of *Helichrysum aureonitens*," *J Ethnopharmacol* 56(2):165-169, Apr. 1997.
Millikan, "The Rationale for Using a Topical Retinoid for Inflammatory Acne," *Am J Clin Dermatol* 4(2):75-80, 2003.
Mohammad Akmal Khan, Qaraabaadeen Azam wa Akmal (20th century AD), Matba Siddiqi, Delhi/Matba Mustafai, Delhi, 1909 AD p. 173, Formulation ID: BA3/1032, Formulation Name: Nuskha Sanoon, 3 pages. (with English translation).
Mohammad Akmal Khan, Qaraabaadeen Azam wa Akmal (20th century AD), Matba Siddiqi, Delhi/Matba Mustafai, Delhi, 1909 AD p. 354, Formulation ID: AH5/199A, Formulation Name: Tila Fasaad-e-Laun, 2 pages. (with Enalish translation).
Mohammad Akmal Khan, Qaraabaadeen Azam wa Akmal (20th century AD), Matba Siddiqi, Delhi/Matba Mustafai, Delhi, 1909 AD p. 410, Formulation ID: AH5/610, Formulation Name: Sanoon Bara-e-Zirs, 3 pages. (with English translation).

(56) References Cited

OTHER PUBLICATIONS

Mohammad Azam Khan, Muheet-e-Azam, vol. III (19$^{th}$ century AD), Matba Nizami, Kanpur, 1887 AD, p. 37, Formulation ID: JA7/36D, Formulation Name: Tila Bara-e Asaraat-e-Harq, 2 pages (with English translation).

Mohammad Najmul Ghani Khan; Qaraabaadeen Najm-al-Ghani (20$^{th}$ century AD), Munshi Nawal Kishore, Lucknow, (Second Edition), 1928 AD p. 667, Formulation ID: NA4/4357, Formulation name: Raughan, 4 pages. (with English translation).

Montine et al., "Antioxidants significantly affect the formation of different classes of isoprostanes and neuroprostanes in rat cerebral synaptosomes," *Biochem Pharmacol* 65(4):611-617, Feb. 15, 2003.

Moore et al., "COX-2 Inhibition, Apoptosis, and Chemoprevention by Nonsteroidal Anti-inflammatory Drugs," *Curr Med Chem* 7(11):1131-1144, 2000.

Morimoto et al., "Effects of *Bofu-tsusho-san*, a traditional Chinese medicine on body fat accumulation in fructose-loaded rats," *Nippon Yakurigaky Zasshi* 117:77-86, 2001. (Abstract only).

Moroney et al., "Selectivity of Neutrophil 5-Lipoxygenase and Cyclo-Oxygenase Inhibition by an Anti-Inflammatory Flavonoid Glycoside and Related Aglycone Flavonoids," *J Pharm Pharmacol* 40(11):787-792, Nov. 1998.

"Move Free Advanced Ingredients—Uniflex," retrieved May 7, 2008, from http://www.movefreeadvanced.com/ingredients. asp?q=unifiex, 3 pages.

Murray et al., "Dietary Supplementation with Vitamin E Reverses the Age-related deficit in Long Term Potentiation in Dentate Gyrus," *J Biol Chem* 273(20):12161-12168, May 15, 1998.

Nagai et al., "Inhibition of Mouse Liver Sialidase by the Root of *Scutellaria baicalensis*," *Plant Medica* 55:27-29, 1989.

Nakahata et al., "Analysis of Inhibitory Effects of Scutellariae Radix and Baicalein on Prostaglandin E$_2$ Production in Rat C6 Glioma Cells," *Am J Chin Med* 26(3-4):311-323, 1998. (English Abstract included).

Nakahata et al., "Inhibition of mitogen-activated protein kinase cascade by baicalein, a flavonoid of natural origin," *Nippon Yakurigaku Zasshi* 114(Supp. 1):215P-219P, 1999.

Nakajima et al., "Inhibitory Effect of Baicalein, a Flavonoid in Scutellaria Root, on Eotaxin Production by Human Dermal Fibroblasts," *Planta Medica* 67(2):132-135, Mar. 2001.

Nakamura, "Arachidonic Acid Cascade Inhibitors Modulate Phorbol Ester-Induced Oxidative Stress In Female ICR Mouse Skin; Differential Roles of 5-Lipoxygenase and Cyclooxygenase-2 in Leukocyte Infiltration and Activation," *Free Radical Biol Med* 35(9):997-1007, Aug. 2003.

Nityanāthasiddhah ; Rasaratnākarah-Rasendra khandam Comm. Datto Vallāl Borakara, Ed. 2$^{nd}$, 1986, Shri Gajānan Book Depot, (Pune), p. 756, Formulation ID: RJ/30, Formulation Name: Kusthaharalepah (02), 3 pages. (with English translation).

Niwa et al., "Application of New Drugs to the Elderly (12)—COX-2 Selective Inhibitor," *Geriatric Gastroenterol* 10(3):181-184, 1998.

Nutracon 2008 NutriAward, retrieved May 1, 2008, from http://www.nutraconference.com/nutraward.index.cfm, 3 pages.

Office Action issued Jul. 19, 2006, for U.S. Appl. No. 10/427,746, 6 pages.

Office Action issued Jan. 4, 2007, for U.S. Appl. No. 10/427,746, 28 pages.

Office Action issued Sep. 21, 2007, for U.S. Appl. No. 10/427,746, 18 pages.

Office Action issued Mar. 21, 2008, for U.S. Appl. No. 10/427,746, 37 pages.

Office Action issued Oct. 30, 2008, for U.S. Appl. No. 10/427,746, 12 pages.

Office Action issued Apr. 13, 2007, for U.S. Appl. No. 10/462,030, 15 pages.

Office Action issued Dec. 21, 2007, for U.S. Appl. No. 10/462,030, 7 pages.

Office Action issued Jul. 15, 2008, for U.S. Appl. No. 10/462,030, 9 pages.

Office Action issued Mar. 5, 2009, for U.S. Appl. No. 10/462,030, 8 pages.

Office Action issued Feb. 9, 2007, for U.S. Appl. No. 10/817,330, 20 pages.

Office Action issued Aug. 7, 2007, for U.S. Appl. No. 10/817,330, 11 pages.

Office Action issued Feb. 20, 2008, for U.S. Appl. No. 10/817,330, 8 pages.

Office Action issued Sep. 3, 2009, for U.S. Appl. No. 10/817,330, 9 pages.

Office Action issued Jan. 10, 2007, for U.S. Appl. No. 10/932,571, 8 pages.

Office Action issued Jun. 27, 2007, for U.S. Appl. No. 10/932,571, 17 pages.

Office Action issued Jun. 15, 2009, for U.S. Appl. No. 11/279,925, 27 pages.

Office Action issued Feb. 8, 2010, for U.S. Appl. No. 11/279,925, 8 pages.

Office Action issued Feb. 26, 2009, for U.S. Appl. No. 11/661,382, 15 pages.

Office Action issued Jan. 2, 2009, for U.S. Appl. No. 11/927,061, 17 pages.

Office Action issued Feb. 13, 2009, for U.S. Appl. No. 11/962,363, 13 pages.

Oringer, "Modulation of the Host Response in Periodontal Therapy," *J Peridontal* 73(4):460-470, Apr. 2002.

Parente, "Pros and Cons of Selective Inhibition of Cyclooxygenase-2 versus Dual Lipoxygenase/Cyclooxygenase Inhibition: Is Two Better than One?," *J Rheumatol* 28:2375-2382, Nov. 2001. (22 pages).

Patrono et al., "Drug Therapy: Low-Dose Aspirin for the Prevention of Atherothrombosis," *New Eng J Med* 353(22):2373-2386, Dec. 2005.

Pelletier et al., "Therapeutic role of dual inhibitors of 5-LOX and COX, selective and non-selective non-steroidal anti-inflammatory drugs," *Ann Rheum Dis* 62:501-509, 2003.

Phillips et al., "Polarized light photography enhances visualization of inflammatory lesions of acne vulgaris," *J Am Acam Dermatol* 37(6):948-952, 1997.

Rae et al., "Leukotriene B$_4$, An Inflammatory Mediator in Gout," *Lancet* 320(8308):1122-1124, Nov. 1982.

Rainsford, "The ever-emerging ant-inflammatories. Have there been any real advances?," *J Physiol—Paris* 95:11-19, 2001.

Raso et al., "Inhibition of inducible nitrix oxide synthase and cyclooxygenase-2 expression by flavonoids in macrophage J774A. 1," *Life Sci* 68(8):921-931, 2001.

Raz et al., "Differential modification of cyclo-oxygenase and peroxidase activities in prostaglandin endoperoxidase synthase by proteolytic digestion and hydroperoxides," *Biochem J* 269(3):603-607, 1990.

Raz et al., "Regulation of Fibroblast Cyclooxygenase Synthesis by Interleukin-1," *J Biol Chem* 263(6):3022-3028, Feb. 25, 1988.

Rioja et al., "An anti-inflammatory ditriazine inhibiting leukocyte functions and expression of inducible nitric oxide synthase and cyclo-oxygenase-2," *Eur J Pharmacol* 397(1):207-217, May 2000.

Rocca et al., "Cyclooxygenase-2 expression is induced during human megakaryopoiesis and characterizes newly formed platelets," *PNAS USA* 99(11):7634-7639, May 2002.

Saleem et al., "Chemistry of the Medicinal Plants of Genus *Acacia*," *Hamdard Medicus* 41(1):63-67, 1998.

Salmon et al., "Evaluation of Inhibitors of Eicosanoid Synthesis in Leukocytes:: Possible Pitfall of Using the Calcium Ionophore A23187 to Stimulate 5' Lipoxygenase," *Prostaglandins* 29(3):377-385, Mar. 1985.

Sartor et al., "Inhibition of matrix-proteases by polyphenols: chemical insights for anti-inflammatory and anti-invasion drug design," *Biochem Pharmacol* 64:229-237, 2002.

Sharon et al., "Production of Leukotrienes by Colonic Mucosa from Patients with Inflammatory Bowel Disease (IBD)," *Gastroenterology* 84(5, Part 2):1306, 1983.

Shen, "Inhibition of thrombin: relevance to anti-thrombosis strategy," *Frontiers Biosci* 11:113-120, Jan. 2006.

(56) References Cited

OTHER PUBLICATIONS

Smalley et al., "Use of Nonsteroidal Anti-inflammatory Drugs and Incidence of Colorectal Cancer," *Arch Intern Med* 159(2):161-166, Jan. 25, 1999.
So et al., "Inhibition of proliferation of estrogen receptor-positive MCF-7 human breast cancer cells by flavonoids in the presence and absence of excess estrogen," *Cancer Letters* 112(2):127-133, Jan. 30, 1997.
Sobottka et al., "Effect of Flavonol Derivatives on the Carrageenin-Induced Paw Edema in the Rat and Inhibition of Cyclooxygenase-1 and 5-Lipoxygenase in Vitro," *Arch Pharm Pharm Med Chem* 333(7):205-210, 2000.
Sodhala; Gadanigrahah ed, Ganga Sahayah Pandeya & Com., Indradeva Tripathi, Part-I(Prayoga Khanda) Chaukhamba Sanskrit Sansthan, Varanasi, Ed. 3rd 1999, p. 107-108, Formulation ID: AK2/158, Formulation Name: Khadiradyam Tailam, 6 pages. (with English translation).
Sodhala; Gadanigrahah ed, Galva Sahayah Pandeya & Com., Indradeva Tripathi, Part-3(Salakya-Pancakarma Khanda) Chaukhamba Sanskrit Sansthan(Varanasi) Ed. 3rd 1999, p. 225, Formulation ID: RG2/525, Formulation Name: Dantasula Cikitsa, 3 pages. (with English translation).
Stadtman et al., "Reactive Oxygen-Mediated Protein Oxidation in Aging and Disease," *Drug Metab Rev* 30:225-243, May 1998.
Stanke-Labesque et al., "Angiotensin II-induced contractions in human internal mammary artery: effects of cyclooxygenase and lipoxygenase inhibition," *Cardiovasc Res* 47:376-383, 2000.
Sugiyama, "The roots of Cha and Gambir," *Yakushigaku Zasshi* 40(20):98-106, 2005. (Abstract only).
Szekanecz et al., "Temporal expression of cytokines and chemokines in rat adjuvant-induced arthritis," *Abstracts of the 21st European Workshop for Rheumatology Research Arthritis Res* 3:A1-A47 Abstract P24, 2001, (47 pages).
Tanaka, "Cosmetics for preventing aging of skin, comprises elastase inhibitor such as catechin, flavones, flavonols, flavanone, isoflavanones, coumarin and/or their glycosides" WPI/Thomson Database, Accession No. 2003-451711 [43], Jan. 8, 2003, 4 pages.
Tordera et al., "Influence of Anti-Inflammatory Flavonoids on Degranulation and Arachidonic Acid Release in Rat Neutrophils," *Z Naturforsch* 49c:235-240, Mar.-Apr. 1994.
Tsao et al., "Effect of Chinese and Western Antimicrobial Agents on Selected Oral Bacteria," *J Dent Res* 61(9):1103-1106, 1982.
Vāgbhata; Astānga Samgraha—(commentary by Indu), Part-I(KA); Central Council for Research in Ayurveda & Siddha, New Delhi, 1991, Time of origin 5-10th Century, p. 27, Formulation ID: AT/2103, Formulation Name: Gandūsadhāranādigunaāh, 3 pages. (with English translation).
Vautrin, "Etude botartique chimique et pharmacaologique du genre *Acacia*. (Botanical, chemical and pharmacological study of the *Acacia* species).," Universitie de Dijon (France) pp. 94, 1996, Abstract #58/646c in *Dissertation Abstracts International* 58(1):177-C, 1997.
Verheugt "New anticoagulants in ischemic heart disease," *Presse Med* 34:1325-1329, Oct. 2005.
Wakabayashi et al., "Wogonin inhibits inducible prostaglandin $E_2$ production in macrophages," *Eur J Pharmacol* 406(3):477-481, Oct. 20, 2000.
Wakdikar, "Global health care challenge: Indian experiences and new prescriptions," *Electronic J Biotechnol* 7(3):217-223, Dec. 15, 2004.
Wallace et al., "Limited anti-inflammatory efficacy of cyclooxygenase-2 inhibition in carrageenan-airpouch inflammation," *Br J Pharmacol* 126:1200-1204, 1999.
Wang et al., "Cyclooxygenase active bioflavonoids from Balaton™ tart cherry and their structure activity relationships," *Phytomedicine* 7(1):15-19, Mar. 2000.
Weinberg, "Nitric Oxide Synthase 2 and Cyclooxygenase 2 Interactions in Inflammation," *Immunol Res* 22(2-3):319-341, 2000.

Wenzel et al., "Dietary Flavone is a Potent Apoptosis Inducer in Human Colon Carcinoma Cells," *Cancer Res* 60(14):3823-3831, Jul. 2000.
Whelton et al., "Cyclooxygenase-2 Specific Inhibitors and Cardiorenal Function: A Randomized, Controlled Trial of Celeeoxib and Rofeeoxib in Older Hypertensive Osteoarthritis Patients," *Am J Ther* 85:85-95, 2001.
Whelton et al., "Nonsteroidal Anti-Inflammatory Drugs: Effects on Kidney Function," *J Clin Pharmcol* 31:588-598, 1991.
Whiteman et al., "Protection Against Peroxynitrite-Dependent Tyrosine Nitration and $\alpha_1$-Antiproteinase Inactivation by Ascorbic Acid. A Comparison with Other Biological Antioxidants," *Free Rad Res* 25(3):275-283, Sep. 1996.
Wikipedia, "Cyclooxygenase," retrieved Sep. 30, 2009, 5 pages.
Wikipedia; "Lipid peroxidation," retrieved Sep. 30, 2009, 2 pages.
Wikipedia, "Peroxidase," retrieved Sep. 30, 2009, 2 pages.
Wilgus et al., "Inhibition of Ultraviolet Light B-induced Cutaneous Inflammation by a Specific Cyclooxygenase-2 Inhibitor," *Adv Exp Med Biol* 507:85-92, 2002.
Wilgus et al., "Topical application of a selective cyclooxygenase inhibitor suppresses UVB mediated cutaneous inflammation," *Prostaglandins & other Lipid Mediators* 62(4):367-384, 2000.
Winter, "Unigen's Univestin targets Joint inflammations," Functional Foods & Neutraceuticals May 2005, p. 14.
Wollheim, "Approaches to rheumatoid arthritis in 2000," *Curr Opin Rheumatol* 13(3):193-201, 2001.
Xiaozhen et al., "Induction of $PGE_2$ Production and COX-2 Expression in Human Gingival Fibroblasts Stimulated with LPS," *Med J Wuhan Uni* 23(4):301-305, Oct. 2002. (with English Abstract).
Xie et al., "Mitogen-Inducible Prostaglandin G/H Synthase: A New Target for Nonsteroidal Antiinflammatory Drugs," *Drug Development Research* 25(4):249-265, 1992.
Yamahara et al., "Inhibitory effect of crude Chinese drugs on the denaturation of human γ-globulin induced by heat and copper (2+)," *Shoyakugaku Zasshi* 35(2):103-107, 1981. (Abstract only).
Yang et al., "Effects of Green Tea Catechin on Phospholipase $A_2$ Activity and Antithrombus in Streptozotocin Diabetic Rats," *J Nutr Sci Vitaminol* 45:337-346, Jun. 1999.
Te et al., "Anticancer Activity of *Sculletaria baicalensis* and Its Potential Mechanism," *J Alt & Complementary Med* 8:567-572, Nov. 5, 2002.
Yoshida et al., "Thermogenic, anti-obesity effects of *bofu-tsusho-san* in MSG-obese mice," *International J Obesity* 19:717-722, 1995.
Yoshimura et al., "Vitamin E Prevents Increase in Oxidative Damage to Lipids and DNA in Liver of ODS Rats Given Total Body X-ray Irradiation," *Free Rad Res* 36(1):107-112, Jan. 2002.
You et al, "Inhibition of Cyclooxygenase/Lipoxygenase from Human Platelets by Polyhydroxylated/Methoxylated Flavonoids Isolated from Medicinal Plants," *Arch Pharm Res* 22(1):18-24, Feb. 1999.
Young et al., "The Mouse Ear Inflammatory Response to Topical Arachidonic Acid," *J Invest Dermatol* 82(4):267-371, 1984.
Zhang et al., "Inhibition of Cancer Cell Proliferation and Prostaglandin $E_2$ Synthesis by *Scutellaria baicalensis*," *Cancer Res* 63:4037-4043, Jul. 15, 2003.
Kalyadeva, Kaiyadevanighantau—(Pathyāpathyavibodhakah), p. 5-9, Ref. p. 153, Edn. 1st. 1979, Chaukhambha Orientalia, Varanasi, India.
Suśruta, Suśruta Samhitā, p. 10-15, Ref p. 461, Edn. 1st. 2000, Chuakhamba Visvabharati, Varanasi, India.
Vāgabhaṭ ta, Aṣṭ stāṅga Hṛ rdaya, p. 16-21, Ref. p. 715, 1998, Chaukhamba Orientalia, Varanasi, India.
Kṛṣṇ rsnarāma Bhatta, Siddhabhe ṣ sajama ṇ nimālāḥ h, p. 17-26, Ref p. 237, Edn. 3rd 2003, Chaukhambha Krishnadas Academy, Varanasi, India.
Mohammad Azam Khan, Ikseer Azam, vol. IV, p. 27-30, Ref. p. 309, 1872 AD, Matba Nizami, Kanpur, India.
Mohammad Akbar Arzani, Qaraabaadeen Qaadri, p. 31-35, Ref. p. 45. 1968 AD, Admadi Publication, Delhi, India.
Bhārata Bhai ṣ sajya Retnākara, p. 36-43, Ref. p. 481, Aug. 1999, B. Jain Publishers, New Delhi, India.

ISOLATION OF A DUAL COX-2 AND 5-LIPOXYGENASE INHIBITOR FROM ACACIA

CROSS REFERENCE TO RELATED APPLICATIONS

This application is a continuation of U.S. application Ser. No. 11/457,388, filed Jul. 13, 2006, now issued as U.S. Pat. No. 8,124,134, which application is a continuation of U.S. application Ser. No. 10/104,477, filed Mar. 22, 2002, now issued as U.S. Pat. No. 7,108,868, which applications are hereby incorporated by reference in their entireties.

FIELD OF THE INVENTION

This invention relates generally to a method for the prevention and treatment diseases and conditions mediated by COX-2 and 5-lipoxygenase. Specifically, the present invention relates to a method for the prevention and treatment of COX-2 and 5-lipoxygenase mediated diseases and conditions by administration of a class of specific compounds, referred to as flavans, extracted from *Acacia* plants. Included in this invention is a method to generate standardized flavan extracts from plant sources.

BACKGROUND OF THE INVENTION

The liberation and metabolism of arachidonic acid (AA) from the cell membrane, results in the generation of pro-inflammatory metabolites by several different pathways. Arguably, two of the most important pathways to inflammation are mediated by the enzymes 5-lipoxygenase (5-LO) and cyclooxygenase (COX). These are parallel pathways that result in the generation of leukotrienes and prostaglandins, respectively, which play important roles in the initiation and progression of the inflammatory response. These vasoactive compounds are chemotaxins, which both promote infiltration of inflammatory cells into tissues and serve to prolong the inflammatory response. Consequently, the enzymes responsible for generating these mediators of inflammation have become the targets for many new drugs aimed at the treatment of inflammation, which that contributes to the pathogenesis of diseases such as rheumatoid arthritis, osteoarthritis, Alzheimer's disease and certain types of cancer.

Inhibition of the enzyme cyclooxygenase (COX) is the mechanism of action attributed to most nonsteroidal anti-inflammatory drugs (NSAIDS). There are two distinct isoforms of the COX enzyme (COX-1 and COX-2) that share approximately 60% sequence homology, but differ in expression profiles and function. COX-1 is a constitutive form of the enzyme that has been linked to the production of physiologically important prostaglandins, which help regulate normal physiological functions, such as platelet aggregation, protection of cell function in the stomach and maintenance of normal kidney function. (Dannhardt and Kiefer (2001) Eur. J. Med. Chem. 36:109-26). The second isoform, COX-2, is a form of the enzyme that is inducible by pro-inflammatory cytokines, such as interleukin-1β (IL-1β) and other growth factors. (Herschmann (1994) Cancer Metastasis Rev. 134: 241-56; Xie et al. (1992) Drugs Dev. Res. 25:249-65). This isoform catalyzes the production of prostaglandin E2 (PGE2) from arachidonic acid (AA). Inhibition of COX-2 is responsible for the anti-inflammatory activities of conventional NSAIDs.

Inhibitors that demonstrate dual specificity for COX-2 and 5-LO while maintaining COX-2 selectivity relative to COX-1 would have the obvious benefit of inhibiting multiple pathways of arachidonic acid metabolism. Such inhibitors would block the inflammatory effects of PGE2, as well as, those of multiple leukotrienes (LT) by limiting their production. This includes the vasodilation, vasopermeability and chemotactic effects of LTB4 and LTD4 and the effects of LTE4, also known as the slow reacting substance of anaphalaxis. Of these, LTB4 has the most potent chemotactic and chemokinetic effects (Moore (1985) *Prostanoids: pharmacological, physiological and clinical relevance*. Cambridge University Press, N.Y., pp. 229-30) and has been shown to be elevated in the gastrointestinal mucosa of patients with inflammatory bowel disease (Sharon and Stenson (1983) Gastroenterology 84:1306-13) and within the synovial fluid of patients with rheumatoid arthritis. (Klicksein et al. (1980) J. Clin. Invest. 66:1166-70; Rae et al. (1982) Lancet ii:1122-4).

In addition to the above-mentioned benefits of dual COX-2/5-LO inhibitors, many dual inhibitors do not cause some of the side effects that are typical of NSAIDs or COX-2 inhibitors, including both the gastrointestinal damage and discomfort caused by traditional NSAIDs. It has been suggested that NSAID induced gastric inflammation is largely due to metabolites of 5-LO, particularly LTB4. (Kircher et al. (1997) Prostaglandins leukotrienes and essential fatty acids 56:417-23). Leukotrienes represent the primary arachidonic acid metabolites within the gastric mucosa following prostanoid inhibition. It appears that these compounds contribute to a significant amount of the gastric epithelial injury resulting from the use of NSAIDs. (Celotti and Laufer (2001) Pharmacological Research 43:429-36). Dual inhibitors of COX and 5-LO were also demonstrated to inhibit the coronary vasoconstriction in arthritic hearts in a rat model. (Gok et al. (2000) Pharmacology 60:41-46). Taken together, these characteristics suggest that there may be distinct advantages to dual inhibitors of COX-2 and 5-LO over COX-2 inhibitors and NSAIDs alone with regard to both increased efficacy and a lack of side effects.

Because the mechanism of action of COX inhibitors overlaps that of most conventional NSAID's, COX inhibitors are used to treat many of the same symptoms, including pain and swelling associated with inflammation in transient conditions and chronic diseases in which inflammation plays a critical role. Transient conditions include treatment of inflammation associated with minor abrasions, sunburn or contact dermatitis, as well as, the relief of pain associated with tension and migraine headaches and menstrual cramps. Applications to chronic conditions include arthritic diseases, such as rheumatoid arthritis and osteoarthritis. Although, rheumatoid arthritis is largely an autoimmune disease and osteoarthritis is caused by the degradation of cartilage in joints, reducing the inflammation associated with each provides a significant increase in the quality of life for those suffering from these diseases. (Wienberg (2001) Immunol. Res. 22:319-41; Wollhiem (2000) Curr. Opin. Rheum. 13:193-201). In addition to rheumatoid arthritis, inflammation is a component of rheumatic diseases in general. Therefore, the use of COX inhibitors has been expanded to include diseases, such as systemic lupus erythromatosus (SLE) (Goebel et al. (1999) Chem. Res. Tox. 12:488-500; Patrono et al. (1985) J. Clin. Invest. 76:1011-1018), as well as, rheumatic skin conditions, such as scleroderma. COX inhibitors are also used for the relief of inflammatory skin conditions that are not of rheumatic origin, such as psoriasis, in which reducing the inflammation resulting from the over production of prostaglandins could provide a direct benefit. (Fogh et al. (1993) Acta Derm Venerologica 73:191-3). Simply stated COX inhibitors are useful for the treatment of symptoms of chronic inflammatory diseases, as well as, the occasional ache and pain resulting from transient inflammation.

In addition to their use as anti-inflammatory agents, another potential role for COX inhibitors is in the treatment of cancer. Over expression of COX-2 has been demonstrated in various human malignancies and inhibitors of COX-2 have been shown to be efficacious in the treatment of animals with skin, breast and bladder tumors. While the mechanism of action is not completely understood, the over expression of COX-2 has been shown to inhibit apoptosis and increase the invasiveness of tumorgenic cell types. (Dempke et al. (2001) J. Can. Res. Clin. Oncol. 127:411-17; Moore and Simmons (2000) Current Med. Chem. 7:1131-44). It is possible that enhanced production of prostaglandins resulting from the over expression of COX-2 promotes cellular proliferation and consequently, increases angiogenesis. (Moore (1985) in *Prostanoids: pharmacological, physiological and clinical relevance*, Cambridge University Press, N.Y., pp. 229-30; Fenton et al. (2001) Am. J. Clin. Oncol. 24:453-57).

There have been a number of clinical studies evaluating COX-2 inhibitors for potential use in the prevention and treatment of different types of cancer. In 1999, 130,000 new cases of colorectal cancer were diagnosed in the U.S. Aspirin, a non-specific NSAID, for example, has been found to reduce the incidence of colorectal cancer by 40-50% (Giovannucci et al. (1995) N Engl J. Med. 333:609-614) and mortality by 50% (Smalley et al. (1999) Arch Intern Med. 159:161-166). In 1999, the FDA approved the COX-2 inhibitor CeleCOXib for use in FAP (Familial Ademonatous Polyposis) to reduce colorectal cancer mortality. It is believed that other cancers, with evidence of COX-2 involvement, may be successfully prevented and/or treated with COX-2 inhibitors including, but not limited to esophageal cancer, head and neck cancer, breast cancer, bladder cancer, cervical cancer, prostate cancer, hepatocellular carcinoma and non-small cell lung cancer. (Jaeckel et al. (2001) Arch. Otolarnygol. 127:1253-59; Kirschenbaum et al. (2001) Urology 58:127-31; Dannhardt and Kiefer (2001) Eur. J. Med. Chem. 36:109-26). COX-2 inhibitors may also prove successful in preventing colon cancer in high-risk patients. There is also evidence that COX-2 inhibitors can prevent or even reverse several types of life-threatening cancers. To date, as many as fifty studies show that COX-2 inhibitors can prevent premalignant and malignant tumors in animals, and possibly prevent bladder, esophageal and skin cancers as well. COX-2 inhibition could prove to be one of the most important preventive medical accomplishments of the century.

Recent scientific progress has identified correlations between COX-2 expression, general inflammation and the pathogenesis of Alzheimer's disease (AD). (Ho et al. (2001) Arch. Neurol. 58:487-92). In animal models, transgenic mice that over express the COX-2 enzyme have neurons that are more susceptible to damage. The National Institute on Aging (NIA) is launching a clinical trial to determine whether NSAIDs can slow the progression of Alzheimer's disease. Naproxen (a non-selective NSAID) and rofecoxib (Vioxx, a COX-2 specific selective NSAID) will be evaluated. Previous evidence has indicated inflammation contributes to Alzheimer's disease. According to the Alzheimer's Association and the NIA, about 4 million people suffer from AD in the U.S.; and this is expected to increase to 14 million by mid-century.

The COX enzyme (also known as prostaglandin H2 synthase) catalyzes two separate reactions. In the first reaction, arachidonic acid is metabolized to form the unstable prostaglandin G2 (PGG2), a cyclooxygenase reaction. In the second reaction, PGG2 is converted to the endoperoxide PGH2, a peroxidase reaction. The short-lived PGH2 non-enzymatically degrades to PGE2. The compounds described herein are the result of a discovery strategy that combined an assay focused on the inhibition of COX-1 and COX-2 peroxidase activity with a chemical dereplication process to identify novel inhibitors of the COX enzymes.

*Acacia* is a genus of leguminous trees and shrubs. The genus *Acacia* includes more than 1000 species belonging to the family of Leguminosae and the subfamily of Mimosoideae. *Acacias* are distributed worldwide in tropical and subtropical areas of central and south America, Africa, parts of Asia, as well as, Australia, which has the largest number of endemic species. *Acacias* occur primarily in dry and arid regions, where the forests are often in the nature of open thorny shrubs. The genus *Acacia* is divided into 3 subgenera based mainly on the leaf morphology—*Acacia, Aculiferum* and *Heterophyllum*. Based on the nature of the leaves of mature trees, however, the genus *Acacia* can be divided into two "popular" groups: the typical bipinnate leaved species and the phyllodenous species. A phyllode is a modified petiole expanded into a leaflike structure with no leaflets, an adaptation to xerophytic conditions. The typical bipinnate leaved species are found primarily throughout the tropics, whereas the phyllodenous species occur mainly in Australia. More than 40 species of *Acacia* have been reported in India. Gamble in his *Flora of Madras Presidency* listed 23 native species for southern India, 15 of which are found in Tamil Nadu. Since that time, many new *Acacia* species have been introduced to India. Approximately 40 species are now found in Tamil Nadu itself. The indigenous species are primarily thorny trees or shrubs and a few are thorny stragglers, such as *A. caesia, A. pennata* and *A. sinuata*. Many species have been introduced from Africa and Australia, i.e. *Acacia mearnsii, A. picnantha* and *A. dealbata*, which have bipinnate leaves and *A. auriculiformis, A. holoserecia* and *A. mangium*, which are phyllodenous species.

*Acacias* are very important economically, providing a source of tannins, gums, timber, fuel and fodder. Tannins, which are isolated primarily from bark, are used extensively for tanning hides and skins. Some *Acacia* barks are also used for flavoring local spirits. Some indigenous species like *A. sinuata* also yield saponins, which are any of various plant glucosides that form soapy lathers when mixed and agitated with water. Saponins are used in detergents, foaming agents and emulsifiers. The flowers of some *Acacia* species are fragrant and used to make perfume. For example, Cassie perfume is obtained from *Acacia ferrugenea*. The heartwood of many *Acacias* is used for making agricultural implements and also provides a source of firewood. *Acacia* gums find extensive use in medicine and confectionary and as sizing and finishing materials in the textile industry. Lac insects can be grown on several species, including *A. nilotica* and *A. catechu*. Some species have been used for forestation of wastelands, including *A. nilotica*, which can withstand some water inundation and a few such areas have become bird sanctuaries.

To date, approximately 330 compounds have been isolated from various *Acacia* species. Flavonoids, a type of water-soluble plant pigments, are the major class of compounds isolated from *Acacias*. Approximately 180 different flavonoids have been identified, 111 of which are flavans. Terpenoids are second largest class of compounds isolated from species of the *Acacia* genus, with 48 compounds having been identified. Other classes of compounds isolated from *Acacia* include, alkaloids (28), amino acids/peptides (20), tannins (16), carbohydrates (15), oxygen heterocycles (15) and aliphatic compounds (10). (Buckingham, *The Combined Chemical Dictionary*, Chapman & Hall CRC, version 5:2, December 2001).

Phenolic compounds, particularly flavans are found in moderate to high concentrations in all *Acacia* species. (Abdulrazak et al. (2000) Journal of Animal Sciences. 13:935-940). Historically, most of the plants and extracts of the *Acacia* genus have been utilized as astringents to treat gastrointestinal disorders, diarrhea and indigestion and to stop bleeding. (Vautrin (1996) Universite Bourgogne (France) European abstract 58-01C:177; Saleem et al. (1998) Hamdard Midicus. 41:63-67). The bark and pods of *Acacia arabica* Willd contain large quantities of tannins and have been utilized as astringents and expectorants. (Nadkarni (1996) India Materia Medica, Bombay Popular Prakashan, pp. 9-17). Diarylpropanol derivatives, isolated from stem bark of *Acacia tortilis* from Somalia, have been reported to have smooth muscle relaxing effects. (Hagos et al. (1987) Planta Medica. 53:27-31, 1987). It has also been reported that terpenoid saponins isolated from *Acacia victoriae* have an inhibitory effect on dimethylbenz(a)anthracene-induced murine skin carcinogenesis (Hanausek et al. (2000) Proceedings American Association for Cancer Research Annual Meeting 41:663) and induce apotosis (Haridas et al. (2000) Proceedings American Association for Cancer Research Annual Meeting. 41:600). Plant extracts from *Acacia nilotica* have been reported to have spasmogenic, vasoconstrictor and antihypertensive activity (Amos et al. (1999) Phytotherapy Research 13:683-685; Gilani et al. (1999) Phytotherapy Research. 13:665-669), and antiplatelet aggregatory activity (Shah et al. (1997) General Pharmacology. 29:251-255). Anti-inflammatory activity has been reported for *A. nilotica*. It was speculated that flavonoids, polysaccharides and organic acids were potential active components. (Dafallah and Al-Mustafa (1996) American Journal of Chinese Medicine. 24:263-269). To date, the only reported 5-lipoxygenase inhibitor isolated from *Acacia* is a monoterpenoidal carboxamide (Seikine et al. (1997) Chemical and Pharmaceutical Bulletin. 45:148-11).

*Acacia* gums have been formulated with other plant ingredients and used for ulcer prevention without identification of any of the active components. (Fuisz, U.S. Pat. No. 5,651,987). *Acacia* gums have also been formulated with other plant ingredients and used to improve drug dissolution (Blank, U.S. Pat. No. 4,946,684), by lowering the viscosity of nutritional compositions (Chancellor, U.S. Pat. No. 5,545,411).

The extract from the bark of *Acacia* has been patented in Japan for external use as a whitening agent (Abe, JP10025238), as a glucosyl transferase inhibitor for dental applications (Abe, JP07242555), as a protein synthesis inhibitor (Fukai, JP 07165598), as an active oxygen scavenging agent for external skin preparations (Honda, JP 07017847, Bindra U.S. Pat. No. 6,126,950), and as a hyaluronidase inhibitor for oral consumption to prevent inflammation, pollinosis and cough (Ogura, JP 07010768).

Catechin is a flavan, found primarily in green tea, having the following structure.

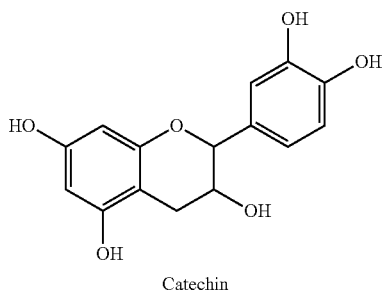 [SMILES: Oc1cc(O)c2c(c1)OC(c1ccc(O)c(O)c1)C(O)C2]

Catechin

Catechin works both alone and in conjunction with other flavonoids found in tea, and has both antiviral and antioxidant activity. Catechin has been shown to be effective in the treatment of viral hepatitis. It also appears to prevent oxidative damage to the heart, kidney, lungs and spleen. Catechin also has been shown to inhibit the growth of stomach cancer cells.

Catechin and its isomer epicatechin inhibit prostaglandin endoperoxide synthase with an $IC_{50}$ value of 40 won. (Kalkbrenner et al. (1992) Pharmacol. 44:1-12). Five flavan-3-ol derivatives, including (+)-catechin and gallocatechin, isolated from four plant species: *Atuna racemosa, Syzygium carynocarpum, Syzygium malaccense* and *Vantanea peruviana*, exhibit equal to weaker inhibitory activity against COX-2, relative to COX-1, with $IC_{50}$ values ranging from 3.3 µM to 138 µM (Noreen et al. (1998) Planta Med. 64:520-524). (+)-Catechin, isolated from the bark of *Ceiba pentandra*, inhibits COX-1 with an $IC_{50}$ value of 80 µM (Noreen et al. (1998) J. Nat. Prod. 61:8-12). Commercially available pure (+)-catechin inhibits COX-1 with an $IC_{50}$ value of around 183 to 279 µM depending upon the experimental conditions, with no selectivity for COX-2. (Noreen et al. (1998) J. Nat. Prod. 61:1-7).

Green tea catechin, when supplemented into the diets of Dawley male rats, lowered the activity level of platelet phospholipase A2 and significantly reduced platelet cyclooxygenase levels. (Yang et al. (1999) J. Nutr. Sci. Vitaminol. 45:337-346). Catechin and epicatechin reportedly weakly suppress COX-2 gene transcription in human colon cancer DLD-1 cells ($IC_{50}$=415.3 µM). (Mutoh et al. (2000) Jpn. J. Cancer Res. 91:686-691). The neuroprotective ability of (+)-catechin from red wine results from the antioxidant properties of catechin, rather than inhibitory effects on intracellular enzymes, such as cyclooxygenase, lipoxygenase, or mitric oxide synthase (Bastianetto et al. (2000) Br. J. Pharmacol. 131:711-720). Catechin derivatives purified from green tea and black tea, such as epigallocatechin-3-gallate (EGCG), epigallocatechin (EGC), epicatechin-3-gallate (ECG), and theaflavins showed inhibition of cyclooxygenase and lipoxygenase dependent metabolism of arachidonic acid in human colon mucosa and colon tumor tissues (Hong et al. (2001) Biochem. Pharmacol. 62:1175-1183) and induce COX-2 expression and PGE(2) production (Park et al. (2001) Biochem. Biophys. Res. Commun. 286:721-725). Epiafzelechin isolated from the aerial parts of *Celastrus orbiculatus* exhibited a dose-dependent inhibition of COX-1 activity with an $IC_{50}$ value of 15 µM and also demonstrated anti-inflammatory activity against carrageenin-induced mouse paw edema following oral administration at a dosage of 100 mg/kg. (Min et al. (1999) Planta Med. 65:460-462).

Catechin and its derivatives from various plant sources, especially from green tea leaves, have been used in the treatment of HPV infected Condyloma acuminata (Cheng, U.S. Pat. No. 5,795,911) and in the treatment of hyperplasia caused by papilloma virus (Cheng, U.S. Pat. Nos. 5,968,973 and 6,197,808). Catechin and its derivatives have also been used topically to inhibit angiogenesis in mammalian tissue, such as skin cancer, psoriasis, spider veins or under eye circles (Anderson, U.S. Pat. No. 6,248,341), against UVB-induced tumorigenesis on mice (Agarwal et al. (1993) Photochem. Photobiol. 58:695-700), for inhibiting nitric oxide synthase at the level of gene expression and enzyme activity (Chan, U.S. Pat. No. 5,922,756), as a hair-growing agent (Takahashi, U.S. Pat. No. 6,126,940). Catechin based compositions have also been formulated with other extracts and vitamins for treatment of acne (Murad U.S. Pat. No. 5,962,517), hardening the tissue of digestive organs (Shi, U.S. Pat. No. 5,470,589), for inhibiting 5 alpha-reductase activity in treating androgenic disorder related diseases and cancers (Liao, U.S. Pat. No. 5,605,929). Green tea extract has been formulated with seven other plant extracts for reducing inflammation by inhibiting the COX-2 enzyme, without identification of any of the specific active components (Mewmark, U.S. Pat. No. 6,264,995).

To date, a number of naturally occurring flavonoids have been commercialized for varying uses. For example, liposome formulations of *Scutellaria* extracts have been utilized for skin care (U.S. Pat. Nos. 5,643,598; 5,443,983). Baicalin has been used for preventing cancer, due to its inhibitory effects on oncogenes (U.S. Pat. No. 6,290,995). Baicalin and other compounds have been used as antiviral, antibacterial and immunomodulating agents (U.S. Pat. No. 6,083,921) and as natural anti-oxidants (Poland Pub. No. 9,849,256). Chrysin has been used for its anxiety reducing properties (U.S. Pat. No. 5,756,538). Anti-inflammatory flavonoids are used for the control and treatment of anorectal and colonic diseases (U.S. Pat. No. 5,858,371), and inhibition of lipoxygenase (U.S. Pat. No. 6,217,875). These compounds are also formulated with glucosamine collagen and other ingredients for repair and maintenance of connective tissue (Bath, U.S. Pat. No. 6,333,304). Flavonoid esters constitute active ingredients for cosmetic compositions (U.S. Pat. No. 6,235,294). The bark, extract and compounds derived from *Phellodendron amurense* have been patented for use in treatment of inflammatory diseases (U.S. Pat. Nos. 5,766,614; 5,908,628; 6,113,909; 6,193,977). Cherry bioflavonoids from *Prunus avium* and *Prunus cerasus* with anthocyanidin type of structures have been patented as cyclooxygenase inhibitors (U.S. Pat. No. 6,194,469, U.S. Pat. Appl. 20010002407).

SUMMARY OF THE INVENTION

The present invention includes methods that are effective in simultaneously inhibiting the enzymes COX-2 and 5-lipoxygenase. The method for simultaneous dual inhibition of the enzymes COX-2 and 5-LO is comprised of administering a composition comprising an individual and/or a mixture of multiple flavans isolated from a single plant or multiple plants in the *Acacia* genus of plants to a host in need thereof.

The present also includes methods for the prevention and treatment of COX-2 and 5-LO mediated diseases and conditions. The method for preventing and treating COX-2 and 5-LO mediated diseases and conditions is comprised of administering to a host in need thereof an effective amount of a composition comprising an individual and/or a mixture of multiple flavans isolated from a single plant or multiple plants in the *Acacia* genus of plants and a pharmaceutically acceptable carrier.

The flavans that can be used in accordance with the following include compounds illustrated by the following general structure:

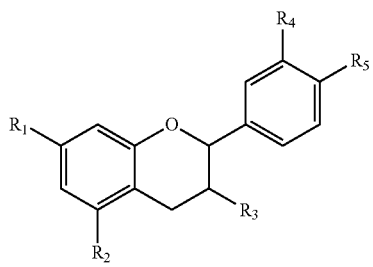

wherein
$R_1$, $R_2$, $R_3$, $R_4$ and $R_5$ are independently selected from the group consisting of H, —OH, —SH, —OCH$_3$, —SCH$_3$, —OR, —SR, —NH$_2$, —NRH, —NR$_2$, —NR$_3^+$X$^-$, esters of the mentioned substitution groups, including, but not limited to, gallate, acetate, cinnamoyl and hydroxyl-cinnamoyl esters, trihydroxybenzoyl esters and caffeoyl esters; thereof carbon, oxygen, nitrogen or sulfur glycoside of a single or a combination of multiple sugars including, but not limited to, aldopentoses, methyl aldopentose, aldohexoses, ketohexose and their chemical derivatives thereof; dimer, trimer and other polymerized flavans;

wherein
R is an alkyl group having between 1-10 carbon atoms; and
X is selected from the group of pharmaceutically acceptable counter anions including, but not limited to hydroxyl, chloride, iodide, sulfate, phosphate, acetate, fluoride, carbonate, etc.

The method of this invention can be used to treat and prevent a number of COX-2 and 5-LO mediated diseases and conditions including, but not limited to, osteoarthritis, rheumatoid arthritis, menstrual cramps, systemic lupus erythromatosus, psoriasis, chronic tension headaches, migraine headaches, topical wound and minor inflammatory conditions, inflammatory bowel disease and solid cancers.

As noted above the flavans of this invention may be obtained from a plant or plants selected from the genus of *Acacia*. In a preferred embodiment, the plant is selected from the group consisting of *Acacia catechu, Acacia concinna, Acacia farnesiana, Acacia Senegal, Acacia speciosa, Acacia arabica, A. caesia, A. pennata, A. sinuata. A. mearnsii, A. picnantha, A. dealbata, A. auriculiformis, A. holoserecia* and *A. mangium*.

The compositions of this invention can be administered by any method known to one of ordinary skill in the art. The modes of administration include, but are not limited to, enteral (oral) administration, parenteral (intravenous, subcutaneous, and intramuscular) administration and topical application. The method of treatment according to this invention comprises administering internally or topically to a patient in need thereof a therapeutically effective amount of the individual and/or a mixture of multiple flavans from a single source or multiple sources that include, but not limited to, synthetically obtained, naturally occurring, or any combination thereof.

The present invention includes a method for isolating and purifying flavans from the *Acacia* genus of plants. The method of the present invention comprises: a) extracting the ground biomass of a plant selected from the *Acacia* genus of plants; b) neutralizing and concentrating said extract; and c) purifying said neutralized and concentrated extract. In a preferred embodiment of the invention the extract is purified using a method selected from the group consisting of recrystallization, precipitation, solvent partition and/or chromatographic separation. The present invention provides a commercially viable process for the isolation and purification of *Acacia* flavans having desirable physiological activity.

The present invention implements a strategy that combines a series of biomolecular screens with a chemical dereplication process to identify active plant extracts and the particular compounds within those extracts that specifically inhibit COX-2 and 5-LO enzymatic activity and inflammation. A total of 1230 plant extracts were screened for their ability to inhibit the peroxidase activity associated with recombinant COX-2. This primary screen identified 22 plant extracts that were further studied for their ability to specifically and selectively inhibit COX-2 in vitro in both cell based and whole blood assays. Those extracts that were efficacious in vitro were then tested for their ability to inhibit inflammation in vivo using a both air pouch and topical ear-swelling models of inflammation when administered by multiple routes (IP and oral). These studies resulted in the discovery of botanical extracts that inhibited COX-2 activity and were efficacious both in vitro and in vivo. These extracts were then tested for their ability to inhibit 5-LO. These studies resulted in the identification of flavan extracts from the *Acacia* genus of plants that demonstrate dual specificity for COX-2 and 5-LO. Applicant believes that this is first report of a composition of matter isolated from the *Acacia* genus of plants that demonstrates this dual specificity for COX-2 and 5-LO.

It is to be understood that both the foregoing general description and the following detailed description are exemplary and explanatory only and are not restrictive of the invention as claimed.

BRIEF DESCRIPTION OF THE FIGURES

FIG. 3C depicts the selected ion chromatogram of HTP fraction D11 at m/z=291 and the structure of the compound catechin.

DETAILED DESCRIPTION OF THE INVENTION

Figure 1:
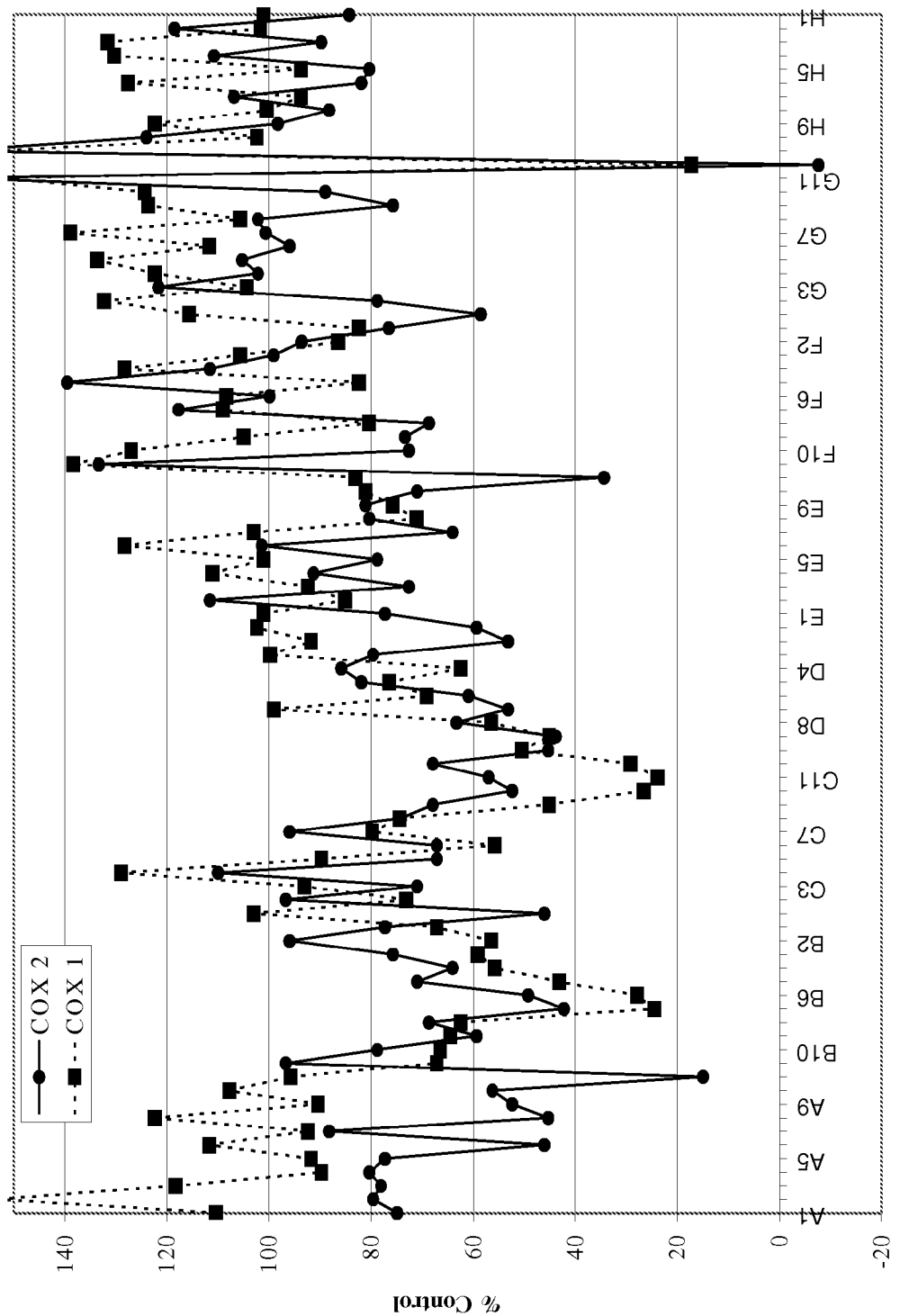
FIG. 1 depicts graphically a profile of the inhibition of COX-1 and COX-2 by HTP fractions from organic extracts of *Acacia catechu*. The extracts were examined for their inhibition of the peroxidase activity of recombinant ovine COX-1 (■) or ovine COX-2 (●). The data is presented as percent of untreated control.

Various terms are used herein to refer to aspects of the present invention. To aid in the clarification of the description of the components of this invention, the following definitions are provided.

"Flavans" are a specific class of flavonoids, which can be generally represented by the following general structure:

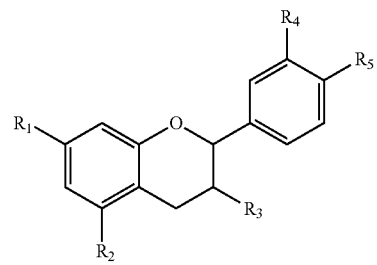

wherein $R_1$, $R_2$, $R_3$, $R_4$ and $R_5$ are independently selected from the group consisting of H, —OH, —SH, —OCH$_3$, —SCH$_3$, —OR, —SR, —NH$_2$, —NRH, —NR$_2$, —NR$_3^+$X$^-$, esters of substitution groups, including, but not limited to, gallate, acetate, cinnamoyl and hydroxyl-cinnamoyl esters, trihydroxybenzoyl esters and caffeoyl esters; thereof carbon, oxygen, nitrogen or sulfur glycoside of a single or a combination of multiple sugars including, but not limited to, aldopentoses, methyl aldopentose, aldohexoses, ketohexose and their chemical derivatives thereof; dimer, trimer and other polymerized flavans;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

"Therapeutic" as used herein, includes treatment and/or prophylaxis. When used, therapeutic refers to humans, as well as, other animals.

"Pharmaceutically or therapeutically effective dose or amount" refers to a dosage level sufficient to induce a desired biological result. That result may be the delivery of a pharmaceutical agent, alleviation of the signs, symptoms or causes of a disease or any other desired alteration of a biological system.

A "host" is a living subject, human or animal, into which the compositions described herein are administered.

Note, that throughout this application various citations are provided. Each citation is specifically incorporated herein in its entirety by reference.

The present invention includes methods that are effective in simultaneously inhibiting both the cyclooxygenase (COX-2) and 5-lipoxygenase (5-LO) enzymes. The method for the simultaneous dual inhibition of the COX-2 and 5-LO enzymes is comprised of administering a composition comprising an individual and/or a mixture of multiple flavans isolated from a single plant or multiple plants selected from the *Acacia* genus of plants to a host in need thereof.

The present also includes methods for the prevention and treatment of COX-2 and 5-LO mediated diseases and conditions. The method for preventing and treating COX-2 and 5-LO mediated diseases and conditions is comprised of administering to a host in need thereof an effective amount of a composition comprising an individual and/or a mixture of multiple flavans isolated from a single plant or multiple plants selected from the *Acacia* genus of plants and a pharmaceutically acceptable carrier.

The flavans that can be used in accordance with the method of this invention include compounds illustrated by the general structure set forth above. The flavans of this invention are isolated from a plant or plants selected from the *Acacia* genus of plants. In a preferred embodiment, the plant is selected from the group consisting of *Acacia catechu, Acacia concinna, Acacia farnesiana, Acacia Senegal, Acacia speciosa, Acacia arabica, A. caesia, A. pennata, A. sinuata. A. mearnsii, A. picnantha, A. dealbata, A. auriculiformis, A. holoserecia* and *A. mangium*.

The flavans can be found in different parts of plants, including but not limited to stems, stem barks, trunks, trunk barks, twigs, tubers, roots, root barks, young shoots, seeds, rhizomes, flowers and other reproductive organs, leaves and other aerial parts.

In order to identify compounds able to inhibit the COX enzymes an extract library composed of 1230 extracts from 615 medicinal plants collected from China, India, and other countries was created. This primary screen identified 22 plant extracts that were further studied for their ability to specifically and selectively inhibit COX-2 in vitro in both cell based and whole blood assays. A general method for preparing the extracts is described in Example 1, which uses the *Acacia catechu* species for purposes of illustration. The ground powder of the bark from *Acacia catechu* was extracted with an organic solvent followed by deionized (DI) water. The extraction process yields an organic and an aqueous extract for each species examined. The results of the extraction are set forth in Table 1. These primary extracts are the source material used in the preliminary assay to identify inhibitors of the cyclooxygenase enzyme's peroxidase activity, which is one of the main functional activities of cyclooxygenase and is responsible for converting PGG2 to PGH2 and ultimately PGE2, as described in detail above. This assay is described in Example 2 and the results are set forth in Table 2. With reference to Table 2, it can be seen that the organic and aqueous extracts from *Acacia catechu* inhibited the peroxidase activity of COX-2 albeit to differing degrees.

The COX-2 inhibitory activity from the primary assay of the crude extracts was confirmed by measurement of dose response and $IC_{50}$ (the concentration required to inhibit 50% of the enzyme's activity). The $IC_{50}$ values are set forth in Table 3. In this assay, *Acacia catechu* organic extract was efficacious ($IC_{50}$=3/6 µg/mL) against human/ovine COX-2 and ovine COX-1 ($IC_{50}$=2.5 µg/mL). Thus, the primary screens for inhibitors of the COX enzyme revealed that the organic extract from *Acacia* genus was efficacious against COX-2 enzyme.

In order to efficiently identify active compounds from plant extracts, a high throughput fractionation process was used, as described in Example 3. Briefly, the organic and aqueous extracts from *Acacia catechu* were fractionated with a high throughput purification system coupled with a due channel broadband UV detector and two Gilson 222XL liquid handlers. Eighty-eight fractions were collected in two 96 deep well plates. Each of the fractions was tested for its ability to inhibit COX activity as per the primary assay, as described in Example 4 and structure dereplication was initialized with the positive HTP fractions with off-line LC/PDA and LC/MS analyses. The results are set forth in FIGS. 1 and 2, which depict the profile of COX-1 and COX-2 inhibition by various HTP fractions derived from the organic and aqueous extracts of *Acacia catechu*, respectively. It should be noted that a number of the HTP fractions actually exhibit selective COX-2 inhibitory activity, suggesting that there are multiple compounds in the extracts that contribute to the observed selective inhibitory effects of the whole extract.

Figure 3A:
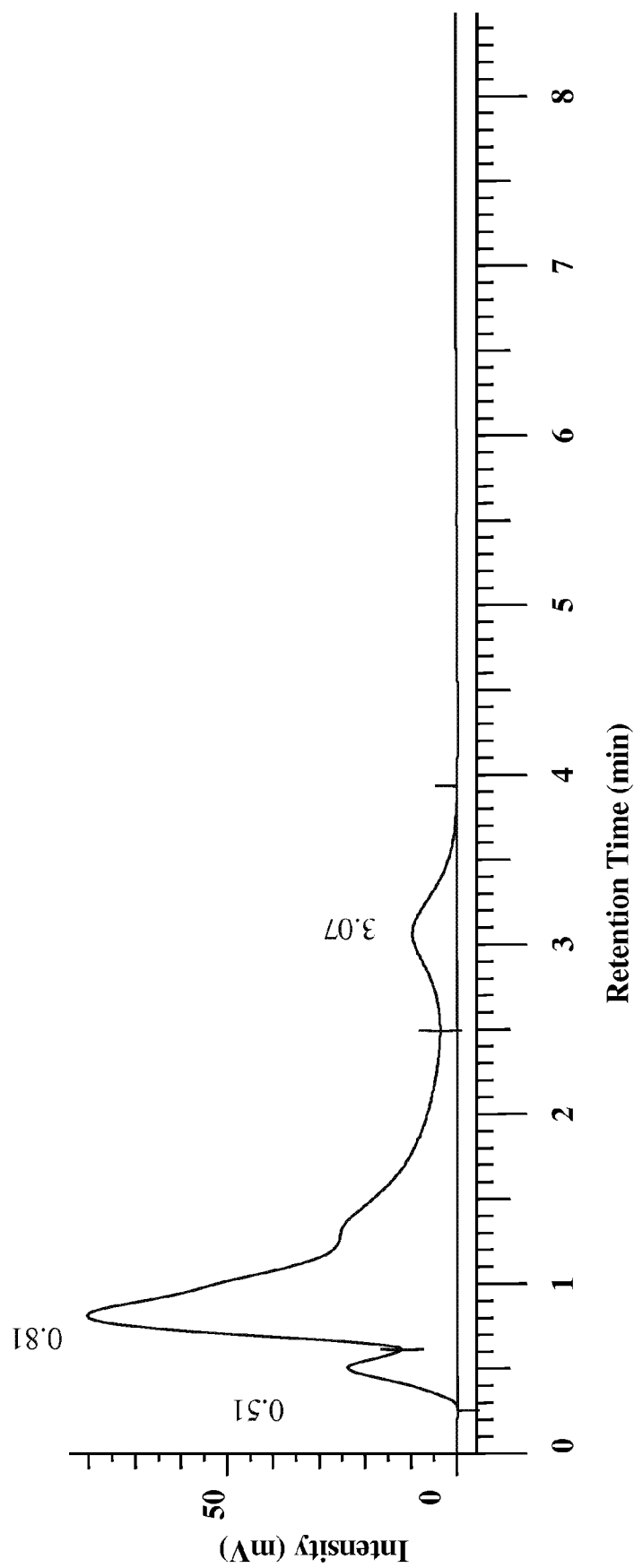
FIG. 3A depicts the LC/PDA chromatogram of HTP fraction D11.
Figure 3B:
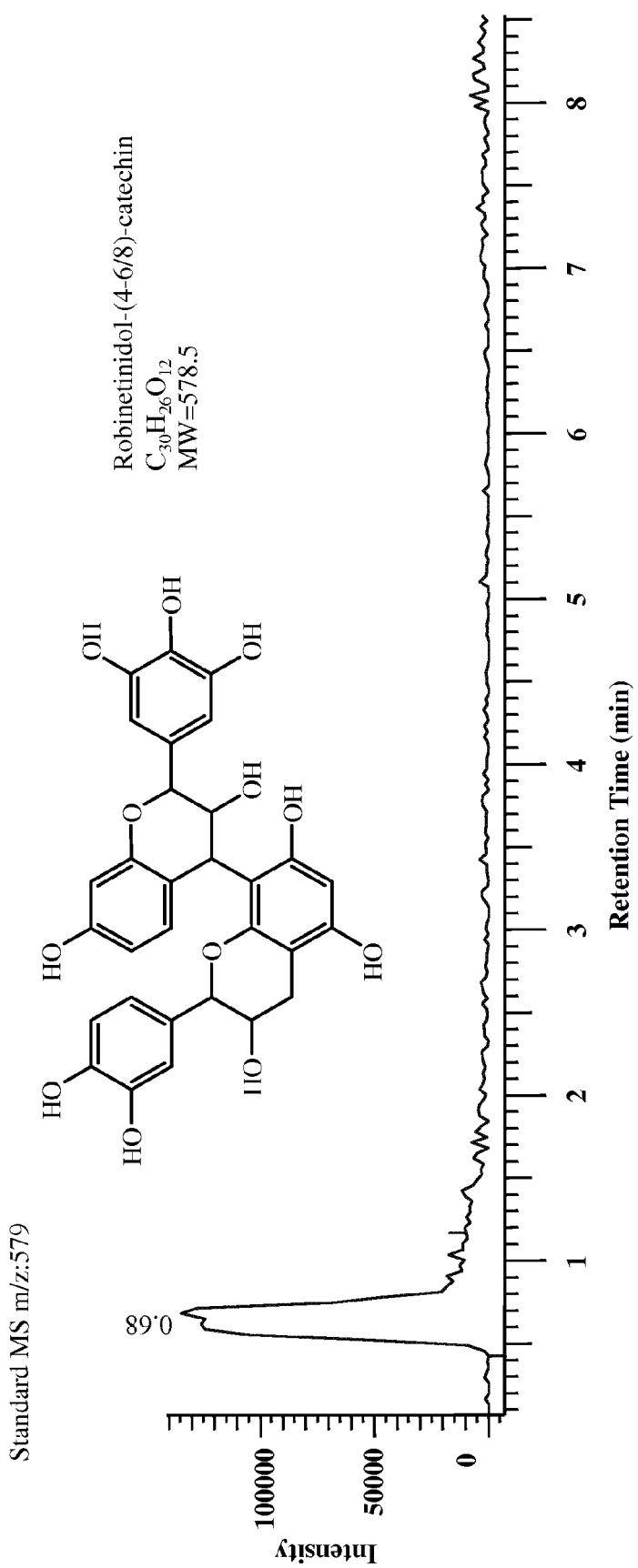
FIG. 3B depicts the selected ion chromatogram of HTP fraction D11 at m/z=579 and the structure of the compound robinetinidol-(4-6/8)-catechin.
Figure 3:
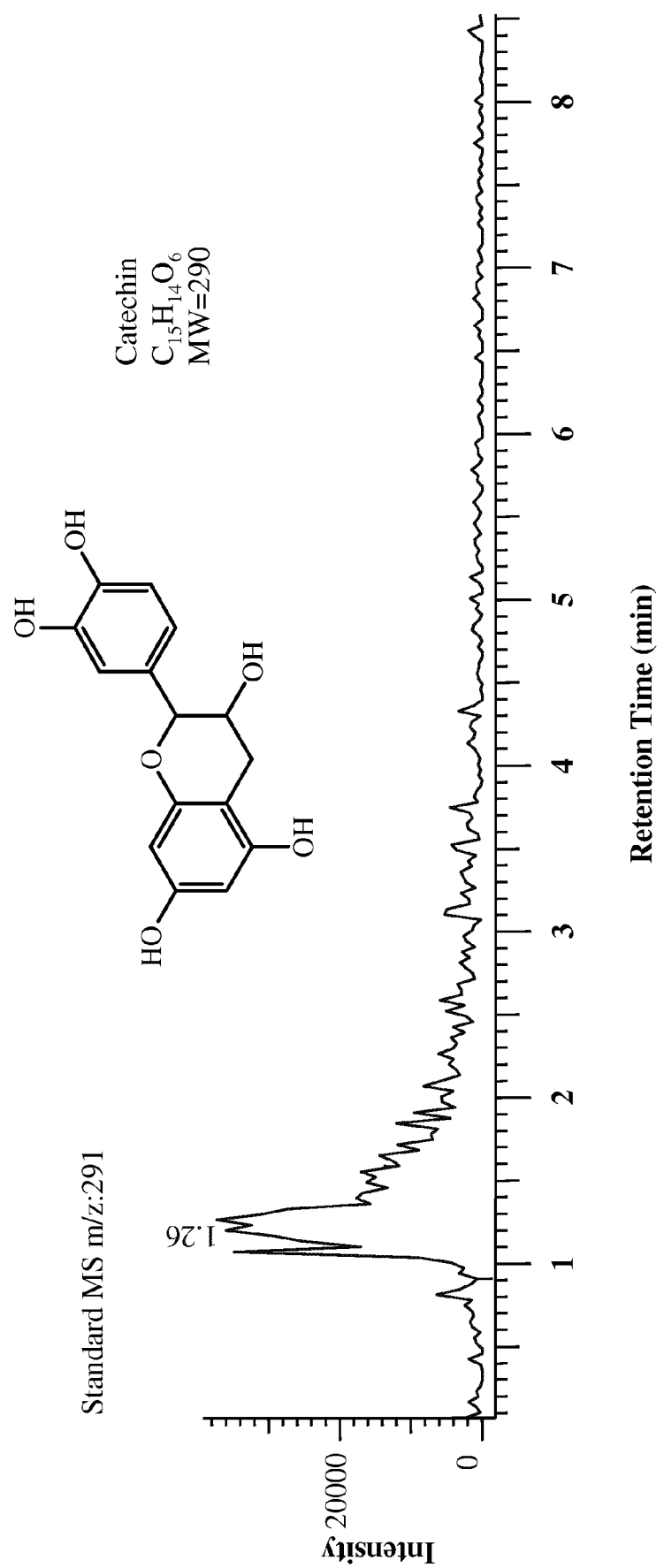
FIG. 3 depicts the results of LC/PDA/MS analysis of active HTP fraction D11, which is described in Example 3.

The active HTP fractions from the aqueous extracts labeled well #C8 to F7 were analyzed using LC/MS with positive mode. The LC/PDA/PDA/MS analysis of fraction D11 are set forth in FIG. 3. The first active peak was located between fractions C9 to D9 and contained catechin components with a [molecular ion+1]$^+$ at 291 m/z. The second active peak, which exhibited COX-1 selectivity, was located between fractions D9 to E2 and contained catechin dimer, having a molecular ion at 578 m/z. The third active peak, which exhibited COX-2 selectivity, was located between fractions #E8 to F8 and contained multiple components with an m/z at 573 & 579, which corresponds to 4-hydroxycinnamoyl-oleanen-3-ol and robinetinidol-catechin, respectively.

The separation, purification and identification of the active components present in the organic extract of *Acacia catechu* is described in Example 5. Using the methodology described in Example 5, catechin and epicatechin were identified as the two major active compounds in the organic extract from the roots of *Acacia catechu*, having $IC_{50}$ values of 5-7 µg/mL.

HPLC quantification of the active extracts from *Acacia catechu* is described in Example 6. The results are set forth in Table 4 which shows that the flavan content in the organic and aqueous extracts, as determined by HPLC, is 30.4% and 1.0%, respectively. This explains why the inhibitory activity of the organic extract is more than twice that of the aqueous extract. HPLC analysis also demonstrates that each extract contains minor flavan components, which contribute to the selective COX-2 inhibitory activity. The HPLC results are set forth in FIGS. 4A and B.

The primary assay described in Example 2 is a cell free system utilizing recombinant enzymes. To further demonstrate the biological activity of the active extracts and compounds, two models that represent cell based in vitro efficacy and animal based in vivo efficacy were employed. The method used to evaluate in vitro efficacy and selectivity is described in Example 7. Two cell lines were selected that could be induced to express primarily COX-1 (THP-1 cells) and COX-2 (HOSC cells), respectively. Each cell type was examined for the production of $PGE_2$, the primary product of the COX enzymes. The results are set forth in Table 5, which shows that the *Acacia* organic extract inhibits both the COX-1 and COX-2 enzymes with a preference for the COX-1 enzyme. While the use of the THP-1 cell line is important and demonstrates the ability of the active compounds to cross the cell membrane, it is an immortalized cell line therefore evaluation of efficacy based on a more relevant model system is desirable. As a result, the extract was also evaluated using whole blood as the primary source of both COX-1 and COX-2 activity. This system measures the inhibition of the production of $PGE_2$ vs. $TXB_2$ to differentiate between COX-2 and COX-1 inhibitory activity, respectively. The results, which are set forth in Table 5, demonstrate that both the COX-1 and COX-2 enzymes are inhibited by the *Acacia* extracts. The $IC_{50}$ values suggest that within this system the *Acacia* extracts are more efficacious against COX-2. Taken as a whole, the inhibitory effect of the active compounds within these extracts is significant and efficacious in both cell free and cell-based systems in vitro.

Figure 5:
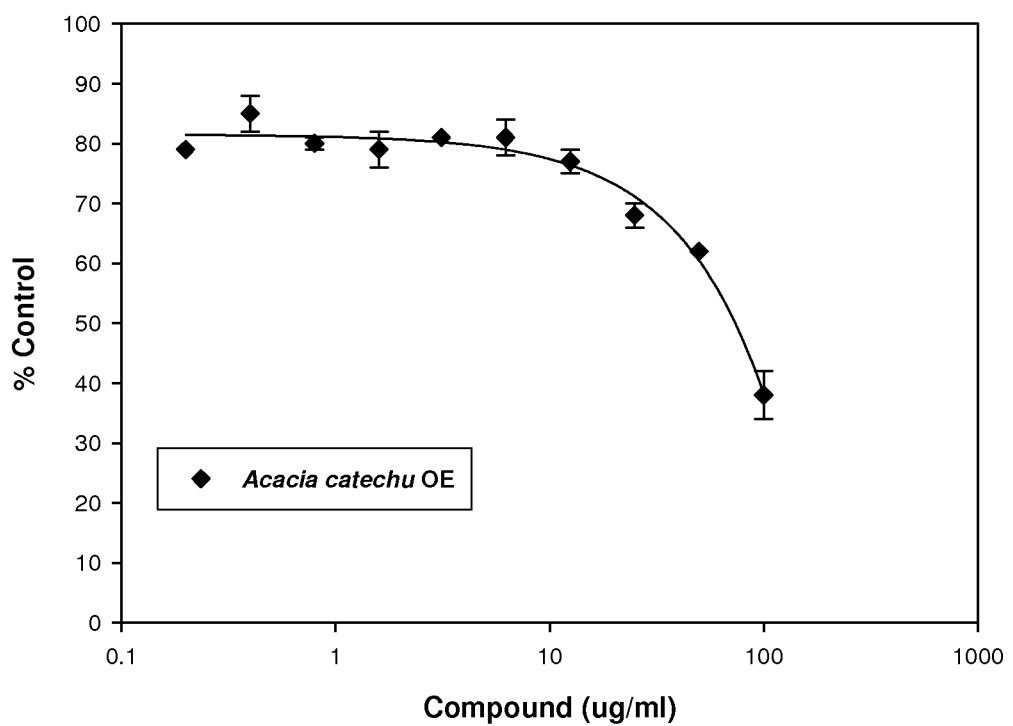
FIG. 5 illustrates graphically the effect of *Acacia catechu* organic extracts on 5-lipoxygenase activity.

As noted above, dual inhibitors of both the COX and 5-LO enzymes have distinct advantages over COX inhibitors alone. These advantages include, but are not limited to, a broader effect on inhibition of arachidonic acid metabolites, a lack of gastrointestinal toxicity and a potential decrease in vasoconstriction. Therefore, the *Acacia* organic extracts were tested for their effects on 5-LO inhibition, as described in Example 8. Briefly, recombinant, human 5-LO was incubated with the *Acacia* extract for 15 minutes prior to the addition of enzyme substrate (umbelliferyl arachidonate). The results are set forth in FIG. 5. The *Acacia* extracts inhibited 5-LO activity in this cell free in vitro system and demonstrated an $IC_{50}$ of 70 μg/mL. Although the $IC_{50}$ of the *Acacia* extracts for 5-LO is higher than that of the same extract for COX-2, it potentially adds a significant benefit for treating inflammation induced by arachidonic acid metabolism.

Two separate in vivo models were employed to determine whether the in vitro efficacy observed from the *Acacia* extracts translated to an ability to inhibit in vivo inflammatory responses. The two models are described in Example 9. The first of these systems is designed to measure inflammation resulting directly from the arachidonic acid metabolism pathway. In this example, mice were treated with extracts from *Acacia* prior to the topical application of AA to the ear to induce the inflammatory response. The effect of pretreating the animals was then measured by the inhibition of the ear swelling using a micrometer. The *Acacia* extracts demonstrated a good inhibitory response suggesting specific inhibition of AA induced inflammatory responses. The results are set forth in FIGS. 6A and 6B. Additionally, the extracts also showed significant inhibition when administered either orally or interperitoneally. Thus, the *Acacia* extracts were demonstrated to be efficacious in reducing inflammation by multiple routes of administration.

The organic extract from *Acacia* was the most efficacious against inflammation induced directly by the arachidonic acid. Therefore, the efficacy of a standardized *Acacia* extract was examined using a second model in which multiple mechanisms of inflammation are ultimately responsible for the final effect. This system is therefore more relevant to naturally occurring inflammatory responses. Using this model, a very potent activator of the complement system is injected into an air pouch created on the back of Balb/C mice. This results in a cascade of inflammatory events including, infiltration of inflammatory cells, activation of COX enzymes, resulting in the release of $PGE_2$, the enzyme myeloperoxidase (MPO), and production of a very specific profile of pro-inflammatory cytokines including TNF-α. These studies demonstrated that even though the *Acacia* did not inhibit the initial infiltration (chemotactic response) of inflammatory cells into the air pouch, it blocked the activation of those cells. This is evidenced by the lack of MPO excreted into the extracellular fluid of the pouch and the noted lack of production of TNF-α. The results are set forth in FIG. 7. The data demonstrates that the *Acacia* extract is efficacious and helps control an inflammatory response in a model system where multiple inflammatory pathways are active. However, the standardized extract produced a toxic effect that was lethal to 60% of the animals receiving the highest concentration of *Acacia* extracts IP (200 mg/kg). This toxic effect was not observed in animals receiving the same dose by gavage.

The preparation of products for administration in pharmaceutical preparations may be performed by a variety of methods well known to those skilled in the art. The flavans may be formulated as an herb powder in the form of its natural existence; as solvent and/or supercritical fluid extracts in different concentrations; as enriched and purified compounds through recrystallization, column separation, solvent partition, precipitation and other means, as a pure and/or a mixture containing substantially purified flavans prepared by synthetic methods.

Various delivery systems are known in the art and can be used to administer the therapeutic compositions of the invention, e.g., aqueous solution, encapsulation in liposomes, microparticles, and microcapsules.

Therapeutic compositions of the invention may be administered parenterally by injection, although other effective administration forms, such as intraarticular injection, inhalant mists, orally active formulations, transdermal iontophoresis or suppositories are also envisioned. One preferred carrier is physiological saline solution, but it is contemplated that other pharmaceutically acceptable carriers may also be used. In one preferred embodiment, it is envisioned that the carrier and flavan(s) constitute a physiologically compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically acceptable excipients for modifying or maintaining the stability, rate of dissolution, release or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder; or directly capsulated and/or tableted with other inert carriers for oral administration. Such formulations may be stored either in a ready to use form or requiring reconstitution immediately prior to administration. The manner of administering formulations containing the compositions for systemic delivery may be via oral, subcutaneous, intramuscular, intravenous, intranasal or vaginal or rectal suppository.

The amount of the composition which will be effective in the treatment of a particular disorder or condition will depend on the nature of the disorder of condition, which can be determined by standard clinical techniques. In addition, in vitro or in vivo assays may optionally be employed to help identify optimal dosage ranges. The precise dose to be employed in the formulation will also depend on the route of administration, and the seriousness or advancement of the disease or condition, and should be decided according to the practitioner and each patient's circumstances. Effective doses may be extrapolated from dose-response curved derived from in vitro or animal model test systems. For example, an effective amount of the composition of the invention is readily determined by administering graded doses of the composition of the invention and observing the desired effect.

The method of treatment according to this invention comprises administering internally or topically to a patient in need thereof a therapeutically effective amount of the individual and/or a mixture of multiple flavans from a single source or multiple sources. The purity of the individual and/or a mixture of multiple flavans includes, but is not limited to 0.01% to 100%, depending on the methodology used to obtain the compound(s). In a preferred embodiment doses of the flavans and pharmaceutical compositions containing the same are an efficacious, nontoxic quantity generally selected from the range of 0.01 to 200 mg/kg of body weight. Persons skilled in the art using routine clinical testing are able to determine optimum doses for the particular ailment being treated.

This invention includes an improved method for isolating and purifying flavans from *Acacia* plants, which is described in Example 10. In Example 10, flavans from *Acacia catechu* were extracted with different solvent systems. The results are set forth in Table 6. The improved method of this invention comprises: extraction of the ground biomass of a plant containing flavans with an organic solvent or a combination of organic solvent(s) and/or water; neutralization and concentration of the neutralized extract; and purification of said extract by recrystallization and/or chromatography. It can be seen from Table 6, that 80% methanol in water is one of the preferred solvents for extraction of flavans from *Acacia* plants. As provided above, these flavans can be can be isolated from the *Acacia* genus of plants. The method of this invention can be extended to the isolation of these compounds from any plant source containing these compounds.

Additionally the flavans can be isolated from various parts of the plant including, but not limited to, the whole plant, stems, stem bark, twigs, tubers, flowers, fruit, roots, root barks, young shoots, seeds, rhizomes and aerial parts. In a preferred embodiment the flavans are isolated from the roots, reproductive organs or the whole plant.

The solvents that can be used for extraction of the ground biomass of the plant include, but are not limited to water, acidified water, water in combination with miscible hydroxylated organic solvent(s) including, but not limited to, methanol or ethanol and an mixture of alcohols with other organic solvent(s) such as THF, acetone, ethyl acetate etc. In one embodiment the extract is neutralized to a pH of 4.5-5.5 and then concentrated and dried to yield a powder. The flavans can then be purified by various methods including, but not limited to recrystallization, solvent partition, precipitation, sublimation, and/or chromatographic methods including, but not limited to, ion exchange chromatography, absorption chromatography, reverse phase chromatography, size exclusive chromatography, ultra-filtration or a combination of two.

The following examples are provided for illustrative purposes only and are not intended to limit the scope of the invention.

EXAMPLES

Example 1

Preparation of Organic and Aqueous Extracts from *Acacia catechu*

Plant material from *Acacia catechu* (L) Willd was ground to a particle size no larger than 2 mm. Dried ground plant material (60 g) was then transferred to an Erlenmeyer flask and methanol:dichloromethane (1:1) (600 mL) was added. The mixture was shaken for one hour, filtered and the biomass was extracted again with methanol:dichloromethane (1:1) (600 mL). The organic extracts were combined and evaporated under vacuum to provide the organic extract (see Table 1 below). After organic extraction, the biomass was air dried and extracted once with ultra pure water (600 mL). The aqueous solution was filtered and freeze-dried to provide the aqueous extract.

TABLE 1

Yield of Organic and Aqueous Extracts of *Acacia catechu*

| Plant Source | Amount | Organic Extract | Aqueous Extract |
|---|---|---|---|
| *Acacia catechu* | 60 g | 27.2 g | 10.8 g |

Example 2

Inhibition of COX-2 and COX-1 Peroxidase Activity by Plant Extracts from *Acacia catechu*

The bioassay directed screening process for the identification of specific COX-2 inhibitors was designed to assay the peroxidase activity of the enzyme as described below.

Peroxidase Assay.

The assay to detect inhibitors of COX-2 was modified for a high throughput platform (Raz and Needleman (1990) J. Biol. Chem. 269:603-607). Briefly, recombinant ovine COX-2 (Cayman) in peroxidase buffer (100 mM, TBS, 5 mM EDTA, 1 µM Heme, 0.01 mg epinephrine, 0.094% phenol) was incubated with the extract (1:500 dilution) for 15 minutes. Quantablu (Pierce) substrate was added and allowed to develop for 45 minutes at 25° C. Luminescence was then read using a Wallac Victor 2 plate reader. The results are set forth in Table 2. The data in Table 2 is presented as the percent of peroxidase activity relative to the recombinant ovine COX-2 enzyme and substrate alone. The percent inhibition ranged from 30% (70% of control) for the aqueous extract to 75% for the organic extract. The data clearly demonstrates that the organic extract is the more efficacious in vitro.

TABLE 2

Inhibition of COX-2 Peroxidase activity by *Acacia catechu*

| Plant Source | Inhibition of COX-2 by organic extract | Inhibition of COX-2 by aqueous extract |
|---|---|---|
| *Acacia catechu* | 75% | 30% |

Comparison of the relative inhibition of the COX-1 and COX-2 isoforms requires the generation of $IC_{50}$ values for each of these enzymes. The $IC_{50}$ is defined as the concentration at which 50% inhibition of enzyme activity in relation to the control is achieved by a particular inhibitor. In the instant case, $IC_{50}$ values were found to range from 3 to 6 µg/mL and 2.5 µg/mL for the COX-2 and COX-1 enzymes, respectively, as set forth in Table 3.

TABLE 3

$IC_{50}$ Values for Human and Ovine COX-2 and COX-1

| Plant Source | $IC_{50}$ Human COX-2 (µg/mL) | $IC_{50}$ Ovine COX-2 (µg/mL) | $IC_{50}$ Ovine COX-1 (µg/mL) |
|---|---|---|---|
| *Acacia catechu* | 3 | 6.25 | 2.5 |

Example 3

HTP Fractionation of Active Extracts

The organic extract (400 mg) from *Acacia catechu* was loaded onto a prepacked flash column. (2 cm ID×8.2 cm, 10 g silica gel). The column was eluted using an Hitachi high throughput purification (HTP) system with a gradient mobile phase of (A) 50:50 EtOAc:hexane and (B) methanol from 100% A to 100% B in 30 minutes at a flow rate of 5 mL/min. The separation was monitored using a broadband wavelength UV detector and the fractions were collected in a 96-deep-well plate at 1.9 mL/well using a Gilson fraction collector. The sample plate was dried under low vacuum and centrifugation. DMSO (1.5 mL) was used to dissolve the samples in each cell and a portion (100 μL) was taken for the COX inhibition assay.

The aqueous extract (750 mg) from *Acacia catechu* was dissolved in water (5 mL), filtered through a 1 μm syringe filter and transferred to a 4 mL HPLC vial. The mixture was then injected by an autosampler onto a prepacked reverse phase column (C-18, 15 μm particle size, 2.5 cm ID×10 cm with precolumn insert). The column was eluted using an Hitachi high throughput purification (HTP) system with a gradient mobile phase of (A) water and (B) methanol from 100% A to 100% B in 20 minutes, followed by 100% methanol for 5 minutes at a flow rate of 10 mL/min. The separation was monitored using a broadband wavelength UV detector and the fractions were collected in a 96-deep-well plate at 1.9 mL/well using a Gilson fraction collector. The sample plate was freeze-dried. Ultra pure water (1.5 mL) was used to dissolve samples in each cell and a portion of 100 μL was taken for the COX inhibition assay. The active HTP fractions from well #C8 to F7 were analyzed with LC/MS/PDA at positive mode with super sonic ionization source. The results for active fraction D11 are set forth in FIG. 3.

Example 4

Inhibition of COX Peroxidase Activity by HTP Fractions from *Acacia catechu*

Figure 2:
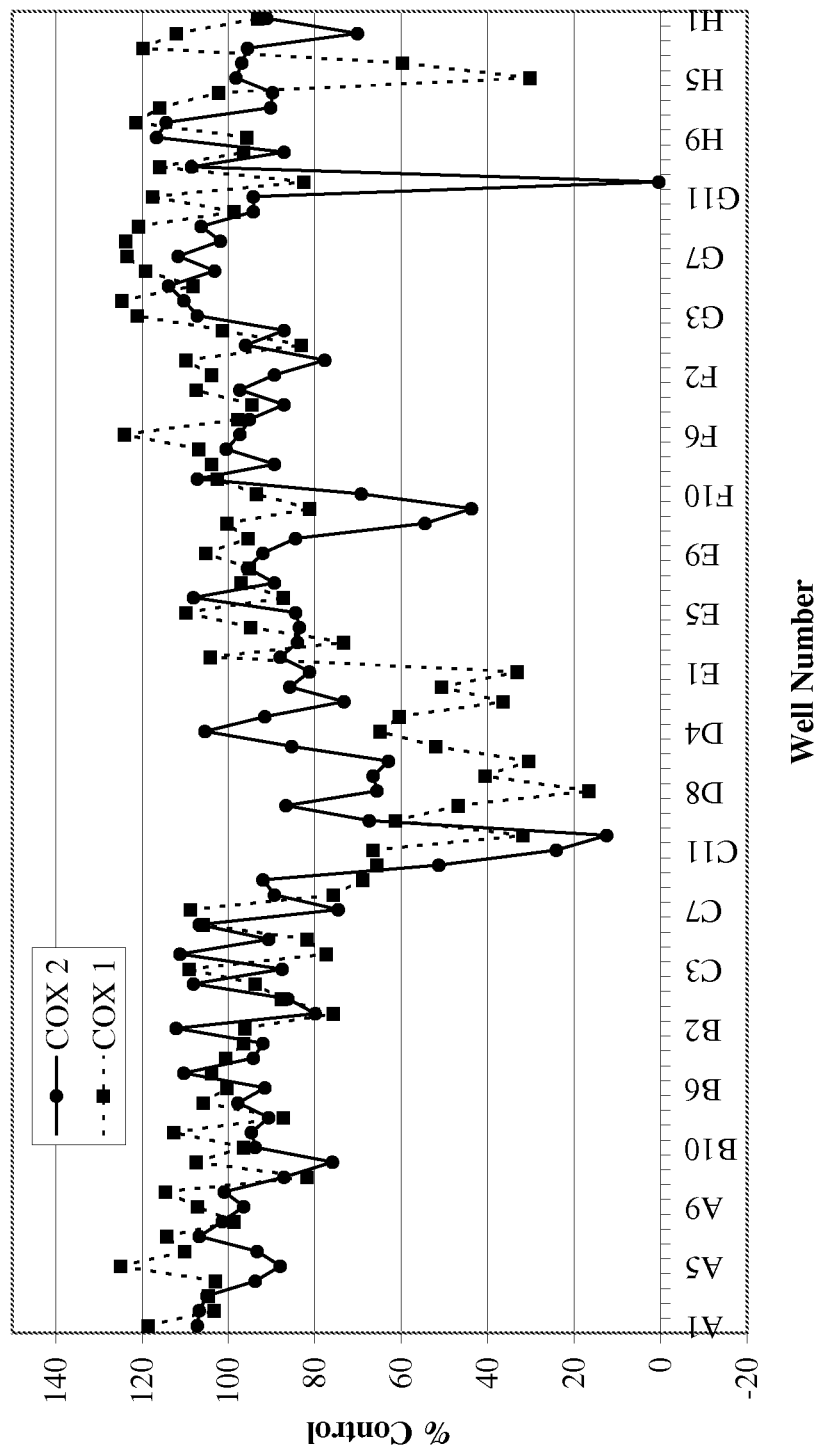
FIG. 2 depicts graphically a profile of the inhibition of COX-1 and COX-2 by HTP fractions from aqueous extracts of *Acacia catechu*. The extracts were examined for their inhibition of the peroxidase activity of recombinant ovine COX-1 (■) or ovine COX-2 (●). The data is presented as percent of untreated control.

Individual organic extracts were further characterized by examining each of the HTP fractions for the ability to inhibit the peroxidase activity of both COX-1 and COX-2 recombinant enzymes. The results are set forth in FIGS. 1 and 2, which depicts the inhibition of COX-2 and COX-1 activity by HTP fractions from *Acacia* isolated as described in Example 1. The profile depicted in FIG. 1 shows a peak of inhibition that is very selective for COX-2 and multiple peaks that inhibit both enzymes with equal efficacy. However, both the COX-1 and COX-2 enzymes demonstrate multiple peaks of inhibition suggesting that there is more than one molecule contributing to the initial inhibition profiles.

Example 5

Isolation and Purification of the Active Compounds from the Organic Extract of *Acacia catechu*

The organic extract (5 g) from the roots of *Acacia catechu*, isolated as described in Example 1, was loaded onto prepacked flash column (120 g silica, 40 μm particle size 32-60 μm, 25 cm×4 cm) and eluted with a gradient mobile phase of (A) 50:50 EtOAc:hexane and (B) methanol from 100% A to 100% B in 60 minutes at a flow rate of 15 mL/min. The fractions were collected in test tubes at 10 mL/fraction. The solvent was evaporated under vacuum and the sample in each fraction was dissolved in DMSO (1 mL) and an aliquot of 20 μL was transferred to a 96 well shallow dish plate and tested for COX inhibitory activity. Based upon the COX assay results, active fractions #32 to #41 were combined and evaporated to yield 2.6 g of solid. Analysis by HPLC/PDA and LC/MS showed two major compounds with retention times of 15.8 and 16.1 minutes, respectively. The product was further purified on a C18 semi-preparatory column (25 cm×1 cm), loaded with 212.4 mg of product and eluted with a gradient mobile phase of (A) water and (B) acetonitrile (ACN), over a period of 60 minutes at a flow rate of 5 mL/minute. Eighty-eight fractions were collected and two active compounds were isolated. Compound 1 (11.5 mg) and Compound 2 (16.6 mg). Purity was determined by HPLC/PDA and LC/MS data by comparison with standards (catechin and epicatechin) and NMR data.

Compound 1.

$^{13}$C NMR: δ ppm (DMSO-d6) 27.84 (C4), 66.27 (C3), 80.96 (C2), 93.78 (C9), 95.05 (C7), 99.00 (C5), 114.48 (C12), 115.01 (C15), 118.36 (C16), 130.55 (C11), 144.79 (C14), 155.31 (C6), 156.12 (C10), 156.41 (C8). $^{1}$H NMR: δ ppm. (DMSO-d6) 9.150 (1H, s, OH), 8.911 (1H, s, OH), 8.835 (1H, s, OH), 8.788 (1H, s, OH), 6.706 (1H, d, J=2 Hz, H2'), 6.670 (1H, d, J=8.0 Hz, H-6'), 6.578 (1H, dd, J=2, 8 Hz, H-5'), 5.873 (1H, d, J=2 Hz, H8), 5.670 (1H, d, J=2 Hz, H6), 4.839 (1H, d, J=4 Hz, OH), 4.461 (1H, d, J=7.3 Hz, H2), 3.798 (1H, m, H3), 2.625 (1H, m, H4b), 2.490 (1H, m, H4a). MS: [M+1]$^{+}$=291 m/e. This compound has been identified as catechin. The IC$_{50}$ values of epicatechin against the COX-1 and COX-2 enzymes are 6 μg/mL and 40 μg/mL, respectively.

Compound 2.

$^{13}$C NMR: δ ppm. (DMSO-d6) 28.17 (C4), 64.87 (C3), 78.02 (C2), 94.03 (C9), 95.02 (C7), 98.44 (C5), 114.70 (C12), 114.85 (C15), 117.90 (C16), 130.56 (C11), 144.39 (C14), 155.72 (C6), 156.19 (C10), 156.48 (C8). $^{1}$H NMR: δ ppm. (DMSO-d6) 9.083 (1H, s, OH), 8.873 (1H, s, OH), 8.777 (1H, s, OH), 8.694 (1H, s, OH), 6.876 (1H, d, J=2 Hz, H2'), 6.646 (2H, s, H-5', 6'), 5.876 (1H, d, J=2 Hz, H8), 5.700 (1H, d, J=2 Hz, H6), 4.718 (1H, s, OH), 4.640 (1H, d, J=4.5 Hz, H2), 3.987 (1H, d, J=4.5 Hz, H3), 2.663 (1H, dd, J=4.6, 6.3 Hz, H4b), 2.463 (1H, dd, J=4.6, 6.3 Hz, H4a). MS: [M+1]$^{+}$=291 m/e. This compound has been identified as epicatechin. The IC$_{50}$ values of epicatechin against the COX-1 and COX-2 enzymes are 7 μg/mL and 20 μg/mL, respectively.

Example 6

HPLC Quantification of Active Extracts from *Acacia catechu*

Figure 4A:
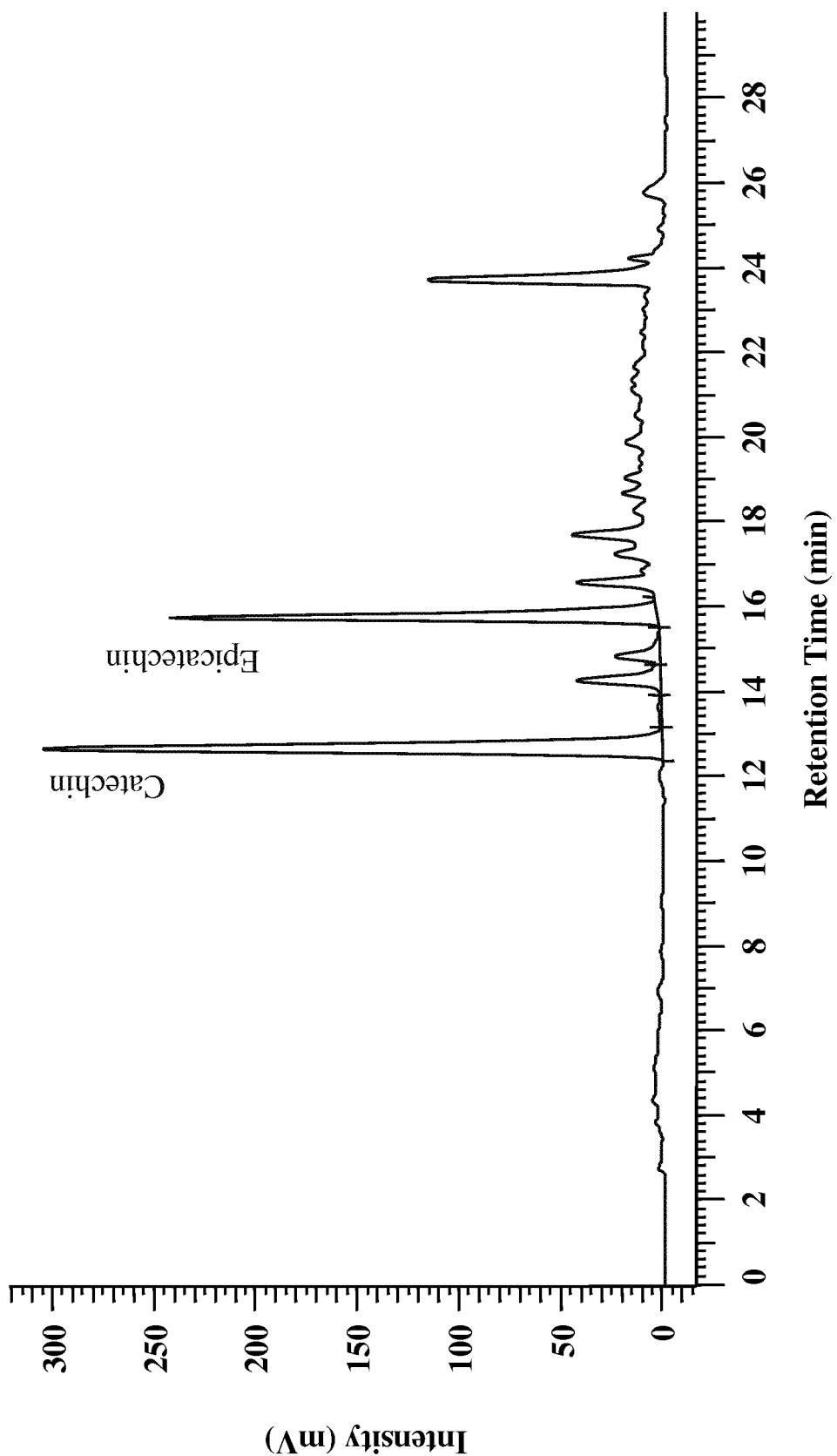
FIG. 4 depicts the high-pressure liquid chromatography (HPLC) traces of the organic (FIG. 4A) and aqueous (FIG. 4B) extracts from *Acacia catechu*.
Figure 4B:
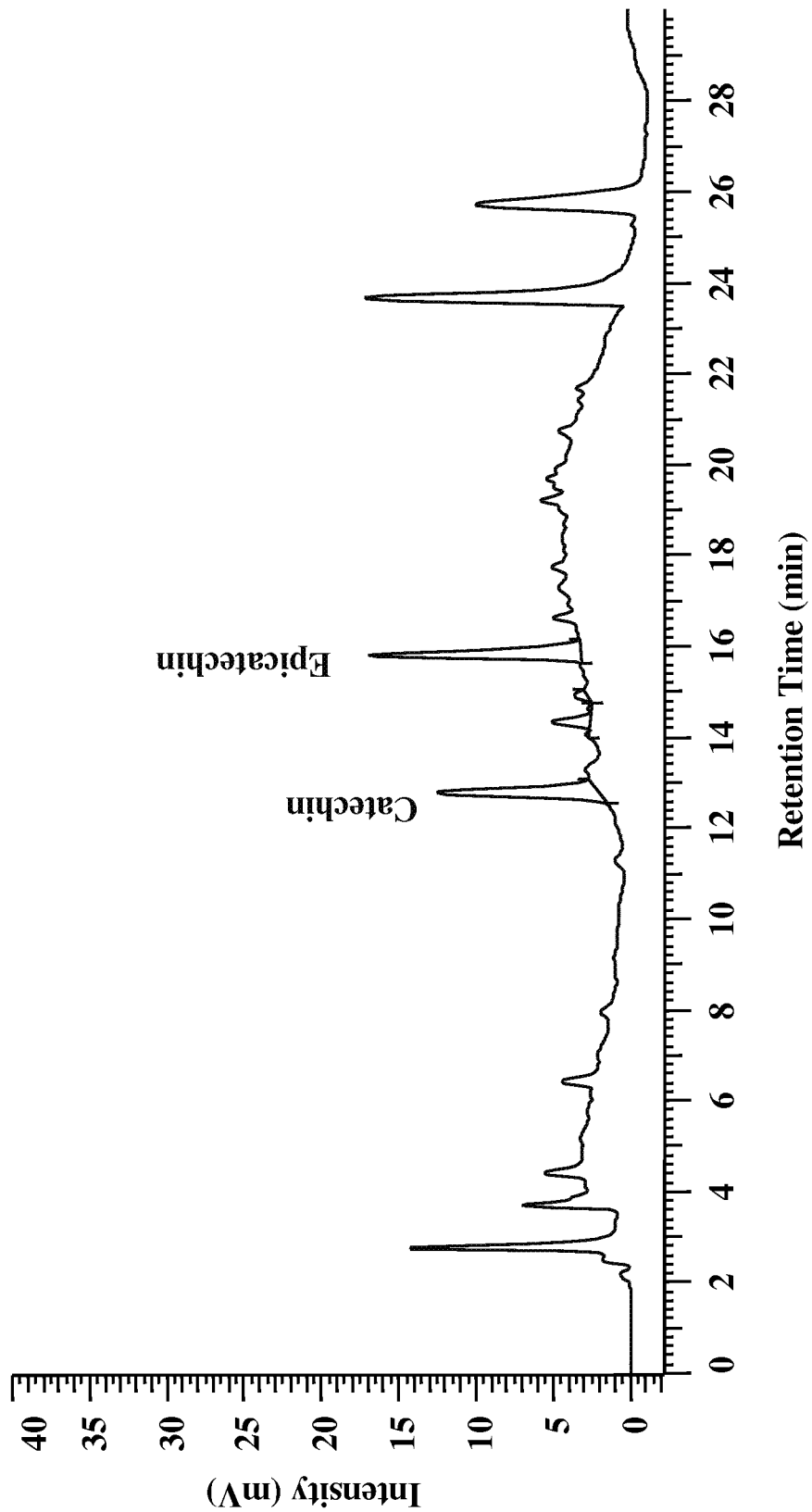

The flavan content in the organic and aqueous extracts from *Acacia catechu* were quantified by High Pressure Liquid Chromatography (HPLC) using a PhotoDiode Array detector (HPLC/PDA) and a Luna C18 column (250 mm×4.6 mm). The flavans were eluted from the column using an acetonitrile gradient from 10% to 30% ACN over a period of 20 minutes, followed by 60% ACN for five minutes. The results are set forth in Table 4. The flavans were quantified based on retention time and PDA data using catechin and epicatechin as standards. The retention times for the two major flavans were 12.73 minutes and 15.76 minutes, respectively. The HPLC chromatograms are depicted in FIGS. 4A and 4B.

TABLE 4

Free-B-Ring Flavonoid Content in Active Plant Extracts

| Active Extracts | Weight of Extract | % Extractible from BioMass | % Flavans in Extract |
|---|---|---|---|
| *Acacia catechu* (AE)* | 10.8 g | 18.0% | 0.998% |
| *Acacia catechu* (OE)* | 27.2 g | 45.3% | 30.37% |

*AE: Aqueous Extract
*OE: Organic Extract

Example 7

In Vitro Study of COX Inhibitory Activity of Organic Extracts from Acacia catechu In vitro efficacy and COX-2 specificity of extracts from Acacia catechu were tested in cell based systems for their ability to inhibit the generation of arachidonic acid metabolites. Cell lines HOSC, which constitutively express COX-2 and THP-1, which express COX-1 were tested for their ability to generate prostaglandin E2 (PGE2) in the presence of arachidonic acid.

COX-2 Cell Based Assay.

HOSC (ATCC#8304-CRL) cells were cultured to 80-90% confluence. The cells were trypsinized, washed and resuspended in 10 mL at $1 \times 10^6$ cells/mL in tissue culture media (MEM). The cell suspension (200 µL) was plated out in 96 well tissue culture plates and incubated for 2 hours at 37° C. and 5% $CO_2$. The media was then replaced with new HOSC media containing 1 ng/mL IL-1b and incubated overnight. The media was removed again and replaced with 190 mL HOSC media. Test compounds were then added in 10 µL of HOSC media and were incubated for 15 minutes at 37° C. Arachidonic acid in HOSC media (20 mL, 100 µM) was added and the mixture was incubated for 10 minutes on a shaker at room temperature. Supernatant (20 µL) was transferred to new plates containing 190 µL/well of 100 µM indomethacin in ELISA buffer. The supernatants were analyzed as described below by ELISA.

COX-1 Cell Based Assay.

THP-1 cells were suspended to a volume of 30 mL ($5 \times 10^5$ cells/mL). TPA was added to a final concentration of 10 nM TPA and cultured for 48 hours to differentiate cells to macrophage (adherent). The cells were resuspended in HBSS (25 mL) and added to 96 well plates in 200 mL volume at $5 \times 10^5$ cells/well. The test compounds in RPMI 1640 (10 µL) were then added and incubated for 15 minutes at 37° C. Arachidonic acid in RPMI (20 µL) was then added and the mixture was incubated for 10 minutes on a shaker at room temperature. Supernatant (20 µL) was added to Elisa buffer (190 µL) containing indomethacin (100 µM). The supernatants were then analyzed by ELISA, as described below.

COX-2 Whole Blood Assay.

Peripheral blood from normal, healthy donors was collected by venipuncture. Whole blood (500 µL) was incubated with test compounds and extracts for 15 minutes at 37° C. Lipopolysaccharide (from E. coli serotype 0111:B4) was added to a final concentration of 100 µg/mL and cultured overnight at 37° C. The blood was centrifuged (12,000×g) and the plasma was collected. Plasma (100 µL) was added to methanol (400 µL) to precipitate proteins. Supernatants were measured for PGE2 production by ELISA. This procedure is a modification of the methods described by Brideau et al. (1996) Inflamm. Res. 45:68-74.

COX-1 Whole Blood Assay.

Fresh blood was collected in tubes not containing anticoagulants and immediately aliquoted into 500 µL aliquots in siliconized microcentrifuge tubes. Test samples were added, vortexed and allowed to clot for 1 hour at 37° C. The samples were then centrifuged (12,000×g) and the plasma was collected. The plasma (100 µL) was added to methanol (400 µL) to precipitate proteins. Supernatants were measured for TXB2 production by ELISA. This procedure is a modification of the methods described by Brideau et al. (1996) Inflamm. Res. 45:68-74.

ELISA Assays.

Immunolon-4 ELISA plates were coated with capture antibody 0.5-4 µg/mL in carbonate buffer (pH 9.2) overnight at 4° C. The plates were washed and incubated for 2 hours with blocking buffer (PBS+1% BSA) at room temperature. The plates were washed again and test sample (100 µL) was added and incubated for 1 hour at room temperature while shaking. Peroxidase conjugated secondary antibody was added in a 50 µL volume containing 0.5-4 mg/mL and incubated for 1 hour at room temperature while shaking. The plates were then washed three times and TMB substrate (100 µL) was added. The plates were allowed to develop for 30 minutes, after which the reaction was stopped by the addition of 1 M phosphoric acid (100 µL). The plates were then read at 450 nm using a Wallac Victor 2 plate reader.

Cytotoxicity.

Cellular cytotoxicity was assessed using a colorimetric kit (Oxford biochemical research) that measures the release of lactate dehydrogenase in damaged cells. Assays were completed according to manufacturers' directions. Both purified flavans and standardized extract from Acacia catechu were tested. No cytotoxicity was observed for any of the tested compounds.

The results of the assays are set forth in Table 5. The data is presented as $IC_{50}$ values for direct comparison. With reference to Table 5, $IC_{50}$ values are generally lower for COX-1 than COX-2. Additionally, whole blood was also measured for the differential inhibition of PGE2 generation (a measure of COX-2 in this system) or thromboxane B2 (TXB2) (a measure of COX 1 activation). Referring to Table 5, these studies clearly demonstrate specificity for COX-2 inhibition within the assays based on whole blood cells. However, studies using the THP-1 and HOSC based model system actually showed greater selectivity for COX-1. Possible reasons for this discrepancy are the fundamental differences between immortalized cell lines that constitutively express each of the enzymes and primary cells derived from whole blood that that are induced to express COX enzymes. Primary cells are the more relevant model to study inflammation in vivo. Additionally, the compounds used to identify COX-1 vs. COX-2 activity vary in each of these systems and consequently are not directly comparable.

TABLE 5

Inhibition of COX Activity in Whole Cell Systems

| | Cell Line Based Assay | | Whole Blood Assay | |
|---|---|---|---|---|
| Plant Source | $IC_{50}$ COX-2 | $IC_{50}$ COX-1 | $IC_{50}$ COX-2 | $IC_{50}$ COX-1 |
| Acacia catechu | 78 µg/mL | 22 µg/mL | 40 µg/mL | >50 µg/mL |

Example 8

Inhibition of 5 Lipoxygenase by the Organic Extracts from Acacia catechu

5-Lipoxygenase Assay.

Human recombinant 5-lipoxygenase enzyme (Cayman) was diluted (1:50) in assay buffer (50 mM Tris-HCl, pH 7.5, 2 mM $CaCl_2$, 1 mM ATP). Equal volumes of sample (1:500 dilution) and diluted enzyme were incubated together while shaking for 15 minutes. Substrate (umbelliferyl arachidonate, 1:5000 in assay buffer) was added and the mixture was incubated for 30 minutes at room temperature while shaking. The resulting luminescence was read using a Wallac Victor 2 plate reader. The results are set forth in FIG. 5.

Example 9

In Vivo Study of COX Inhibitory Activity of Organic Extracts from *Acacia catechu*

In vivo inhibition of inflammation was measured using two model systems. The first system (ear swelling model) measures inflammation induced directly by arachidonic acid. This is an excellent measure of COX-2 inhibition, but does not measure any of the cellular events which occur upstream of arachidonic acid liberation from cell membrane phospholipids by phospholipase A2 (PLA2). Therefore, to determine how inhibitors function in a more biologically relevant response the air pouch model was employed. This model utilizes a strong activator of complement to induce an inflammatory response that is characterized by a strong cellular infiltrate and inflammatory mediator production including cytokines as well as arachidonic acid metabolites.

Ear Swelling Model.

Figure 6A:
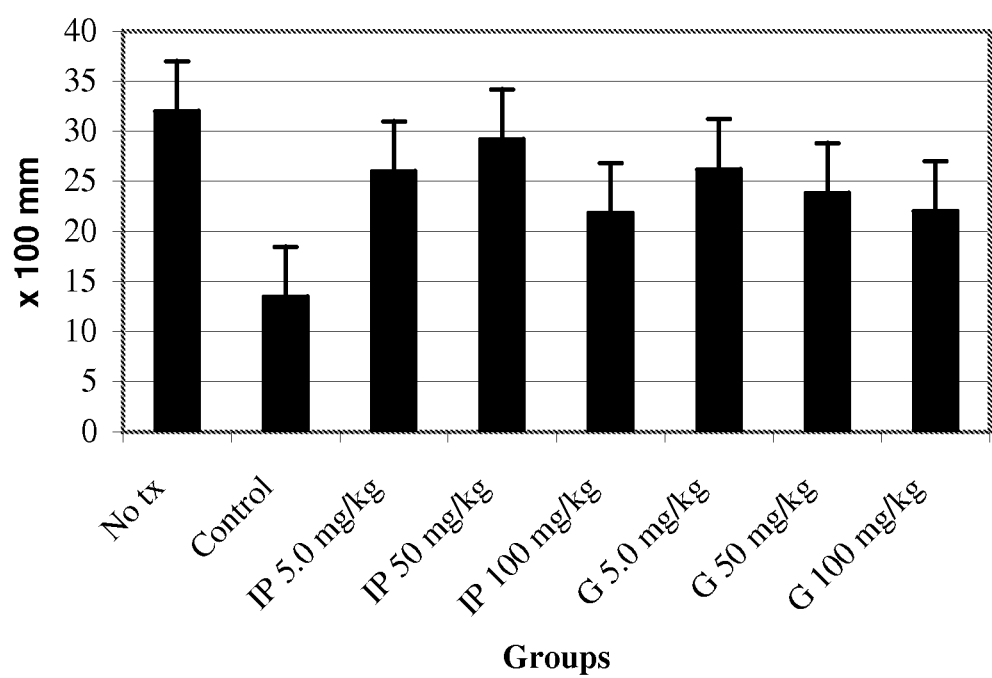
FIG. 6 illustrates the inhibition of arachidonic acid induced inflammation by *Acacia catechu*. The in vivo efficacy was evaluated based on the ability to inhibit swelling induced by direct application of arachidonic acid as described in Example 9. The average difference in swelling between treated ears and control ears is depicted in FIG. 6A.
FIG. 6B depicts the percent inhibition of each group in comparison to the arachidonic acid treated control.
Figure 6B:
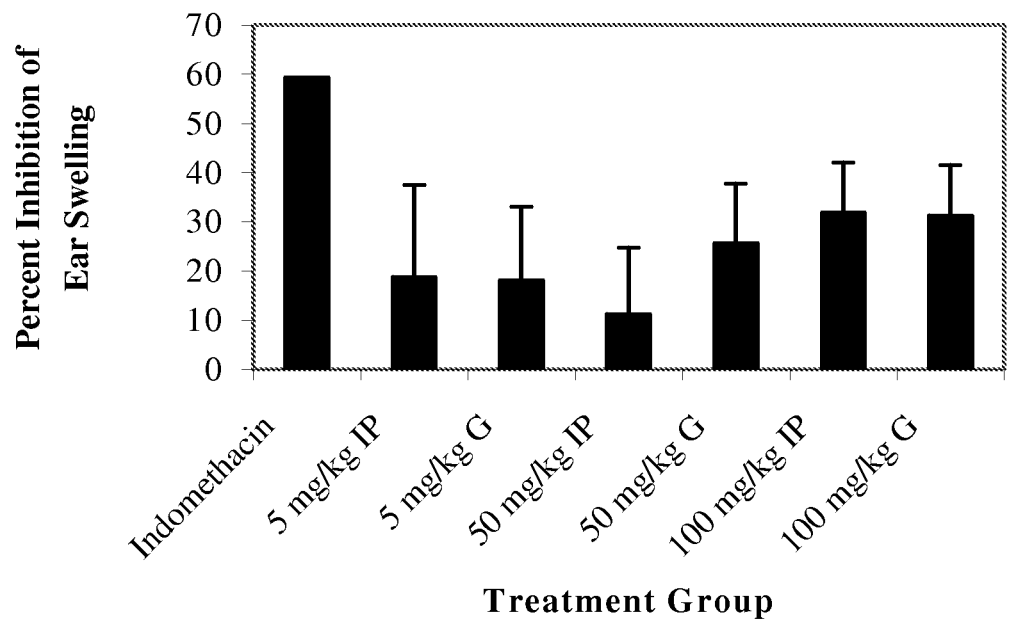

The ear swelling model is a direct measure of the inhibition of arachidonic acid metabolism. Briefly, arachidonic acid in acetone is applied topically to the ears of mice. The metabolism of arachidonic acid results in the production of proinflammatory mediators produced by the action of enzymes such as COX-2. Inhibition of the swelling is a direct measure of the inhibition of the enzymes involved in this pathway. The results are set forth in FIG. 6, which shows the effects of the extracts delivered either orally by gavage or interperitoneally (IP) at two time points (24 hours and 1 hour). Extracts from *Acacia* inhibited swelling when delivered by both IP and gavage (FIG. 6A and FIG. 6B).

Air Pouch Model.

Because *Acacia* organic extracts were efficacious in the ear swelling model a standardized *Acacia* extract was also examined using the air pouch model of inflammation. Briefly, an air pouch was created on the back of mice by injecting 3 mL of sterile air. The air pouch was maintained by additional injections of 1 mL of sterile air every other day for a period of one week. Animals were dosed using the same methods and concentrations described for the ear-swelling model and injected with Zymosan (into the air pouch) to initiate the inflammatory response. After four hours, the fluid within the pouch was collected and measured for the infiltration of inflammatory cells, myeloperoxidase (MPO) activity (a measure of cellular activation, degranulation). The results are set forth in FIG. 7.

Figure 7A:
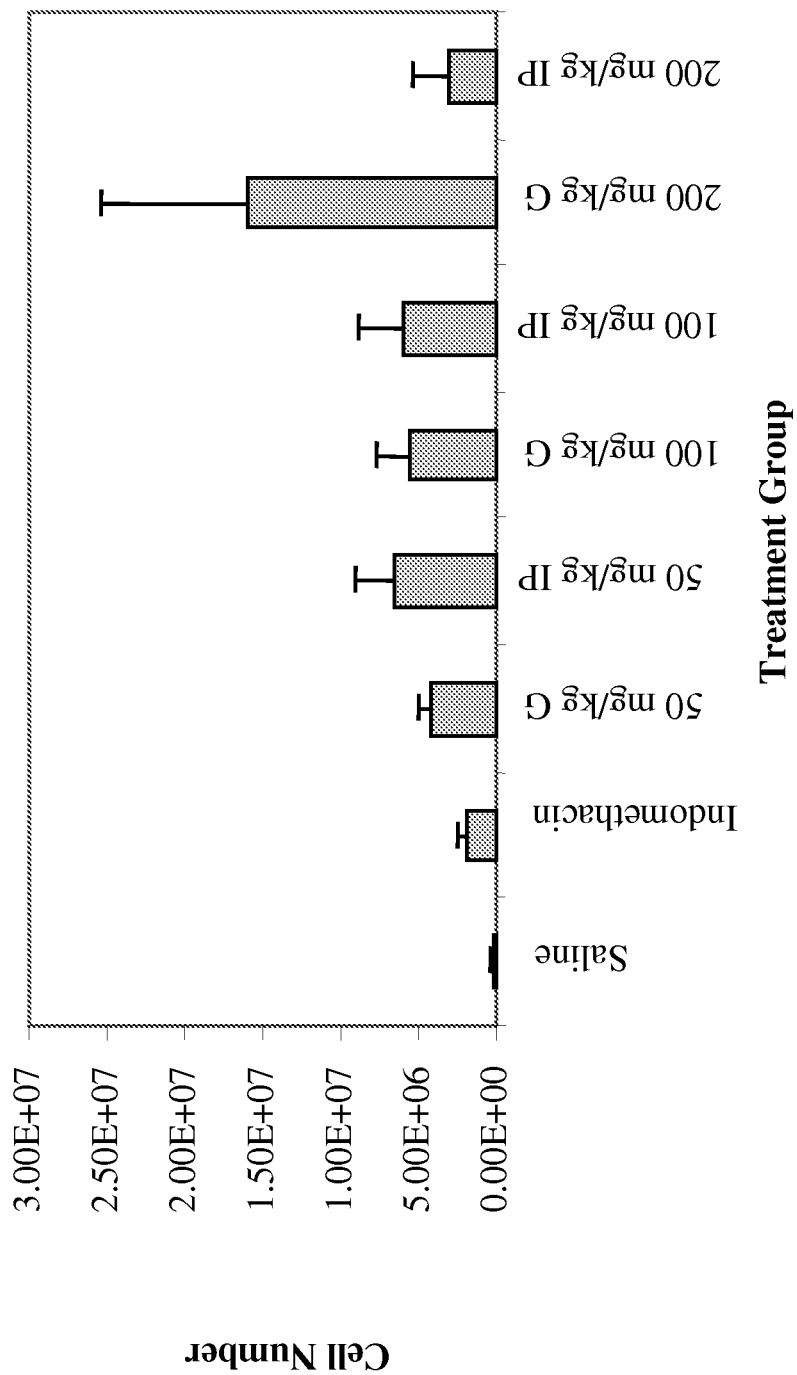
FIG. 7 illustrates the effect of standardized *Acacia* extracts on Zymosan induced inflammation. Zymosan was used to elicit a pro-inflammatory response in an air pouch as described in Example 9. Markers of inflammation including infiltration of pro-inflammatory cells (FIG. 7A), MPO concentrations under different experimental conditions (FIG. 7B) and percent inhibition of MPO activity within the air pouch fluid (FIG. 7C) were used to evaluate the efficacy and mechanism of action of the anti-inflammatory activity of *Acacia* extracts.
Figure 7B:
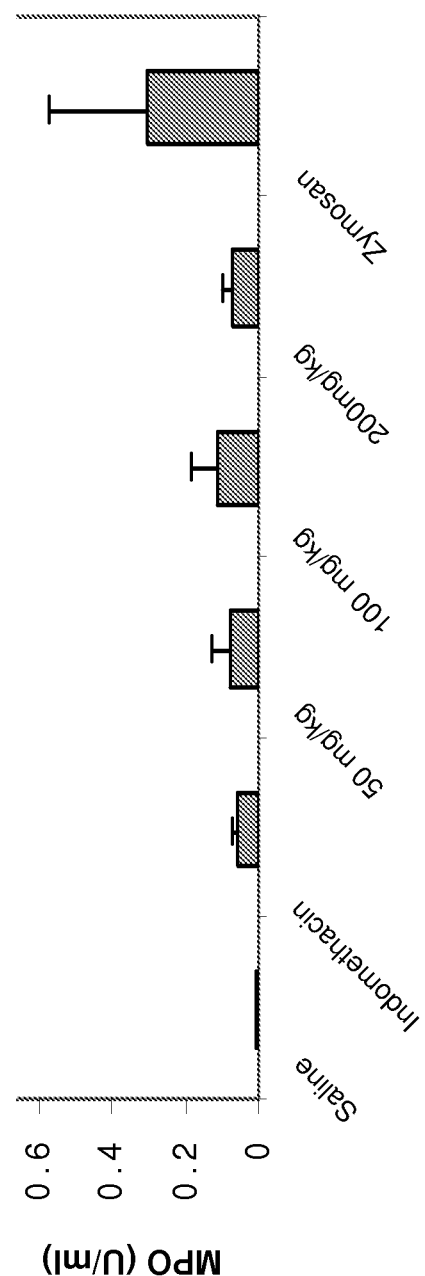
Figure 7C:
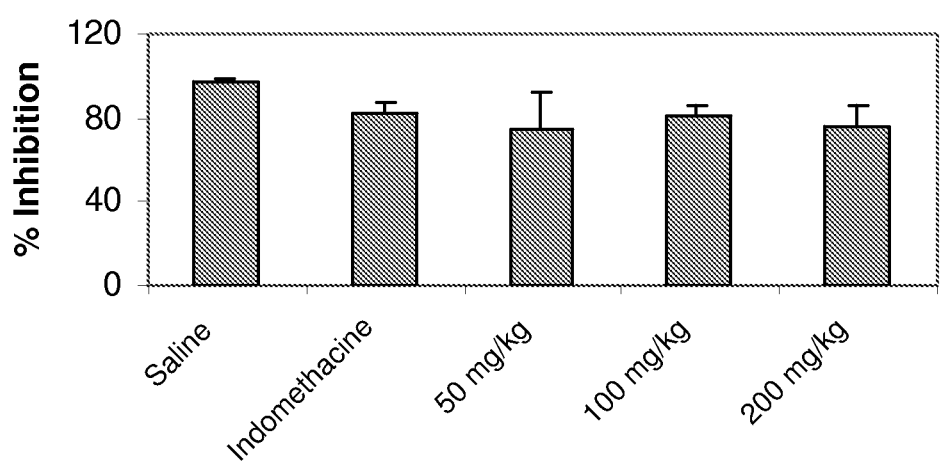

FIG. 7A shows the total number of cells collected from the air pouch fluid. While there was a strong response that was inhibited by controls (indomethacin), the standardized *Acacia* extract did not inhibit the infiltration of the inflammatory cells (chemotaxis). Even though the chemotactic response was not diminished, the fluid was examined to determine whether the infiltrating cells have become activated by measuring MPO activity. FIGS. 7B and 7C demonstrate that MPO activity is significantly reduced when the extract is administered IP, but not by gavage. These data suggest that although the extracts do not inhibit the chemotactic response induced by complement activation, they are still effective at reducing inflammation through the prevention of release and production of pro-inflammatory mediators.

Arachidonic Acid Induced Ear Swelling.

The ability of *Acacia* extracts to directly inhibit inflammation in vivo was measured as previously described. (Greenspan et al. (1999) J. Med. Chem. 42:164-172; Young et al. (1984) J. Invest. Dermat. 82:367-371). Briefly, groups of 5 Balb/C mice were given dosages of test compounds either interperitoneally (I.P.) or orally by gavage, 24 hours and 1 hour prior to the application of arachidonic acid (AA). AA in acetone (2 mg/15 µL) was applied to the left ear, and acetone (15 µL) as a negative control was applied to the right ear. After 1 hour the animals were sacrificed by $CO_2$ inhalation and the thickness of the ears was measured using an engineer's micrometer. Controls included animals given AA, but not treated with anti-inflammatory agents and animals treated with AA and indomethacin (I.P.) at 5 mg/kg.

Air Pouch Model of Inflammation.

Air pouch models were adapted from the methods of Rioja et al. (2000) Eur. J. Pharm. 397:207-217. Air pouches were established in groups of 5 Balb/C mice by injection of sterile air (3 mL) and maintained by additional injections of 1 mL every 2 days for a period of six days. Animals were given dosages of test compounds either I.P. or orally by gavage, 24 hours and 1 hour prior to the injection of 1% Zymosan (1 mL) into the pouch. After 4 hours, the animals were sacrificed by $CO_2$ inhalation and the air pouches were lavaged with sterile saline (3 mL). The lavage fluid was centrifuged and the total number of infiltrating cells determined. Supernatants were also retained and analyzed for myeloperoxidase (MPO) activity and the presence of TNF-α by ELISA as measures of activation.

Example 10

Development a Standardized Extract from *Acacia catechu*

Figure 8:
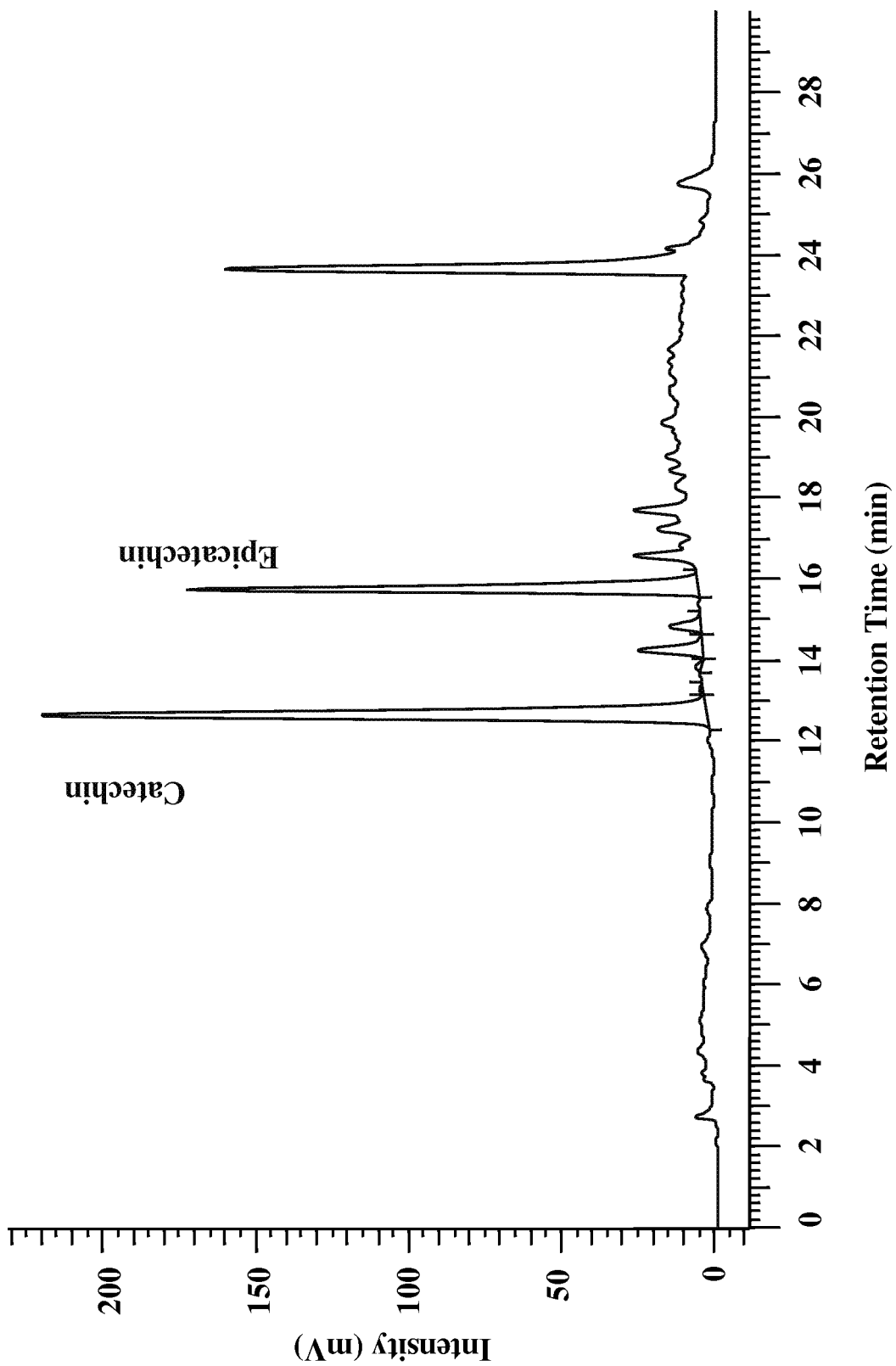
FIG. 8 depicts the HPLC tract of the flavans extracted from *Acacia catechu* with 80% MeOH in water.

*Acacia catechu* (500 mg of ground bark) was extracted with the following solvent systems. (1) 100% water, (2) 80:20 water:methanol, (3) 60:40 water:methanol, (4) 40:60 water:methanol, (5) 20:80 water:methanol, (6) 100% methanol, (7) 80:20 methanol:THF, (8) 60:40 methanol:THF. The extract was concentrated and dried under low vacuum. Identification of the chemical components was carried out by High Pressure Liquid Chromatography using a PhotoDiode Array detector (HPLC/PDA) and a 250 mm×4.6 mm C18 column. The chemical components were quantified based on retention time and PDA data using catechin and epicatechin as standards. The results are set forth in Table 6 and FIG. 8. As shown in Table 6 and FIG. 8, the flavan extract generated from solvent extraction with 80% methanol/water provided the best concentration of flavan components.

TABLE 6

Solvents for Generating Standardized Flavan Extracts from *Acacia catechu*

| Extraction Solvent | Weight of Extract | % Extractible from BioMass | Total amount of Catechins | % Catechins in Extract |
|---|---|---|---|---|
| 100% water | 292.8 mg | 58.56% | 0.13 mg | 12.02% |
| water:methanol (80:20) | 282.9 mg | 56.58% | 0.13 mg | 11.19% |
| water:methanol (60:40) | 287.6 mg | 57.52% | 0.15 mg | 13.54% |
| water:methanol (40:60) | 264.8 mg | 52.96% | 0.19 mg | 13.70% |
| water:methanol (20:80) | 222.8 mg | 44.56% | 0.15 mg | 14.83% |
| 100% methanol | 215.0 mg | 43.00% | 0.15 mg | 12.73% |
| methanol:THF (80:20) | 264.4 mg | 52.88% | 0.11 mg | 8.81% |
| methanol:THF (60:40) | 259.9 mg | 51.98% | 0.15 mg | 9.05% |

The invention claimed is:

1. A method for alleviating pain, comprising administering to a human or animal in need thereof a therapeutically effective amount of an *Acacia* extract enriched for catechin and epicatechin, wherein the method alleviates cyclooxygenase and 5-lipoxygenase mediated inflammation in the human or animal.

2. The method according to claim 1, wherein the *Acacia* is selected from *Acacia catechu, Acacia concinna, Acacia farnesiana, Acacia senegal, Acacia speciosa, Acacia arabica, Acacia caesia, Acacia pennata, Acacia sinuata, Acacia mearnsii, Acacia picnantha, Acacia dealbata, Acacia auriculiformis, Acacia holoserecia,* or *Acacia mangium*.

3. The method according to claim 1, wherein the extract is from an *Acacia* plant part selected from the group consisting of stems, stem barks, trunks, trunk barks, twigs, tubers, roots, root barks, young shoots, seeds, rhizomes, flowers and other reproductive organs, leaves and other aerial parts.

4. The method according to claim 1, wherein the pain associated with the cyclooxygenase and 5-lipoxygenase mediated inflammation is selected from the group consisting of osteoarthritis, rheumatoid arthritis, menstrual cramps, systemic lupus erythematosis, psoriasis, chronic tension headache, migraine headaches, inflammatory bowel disease; topical wounds, minor abrasions, sunburn, contact dermatitis, and solid cancers.

5. The method according to claim 1, wherein the *Acacia* extract is comprised of 0.01% to 100% of flavans.

6. The method according to claim 1, wherein the *Acacia* extract is administered at a dose of 0.01 to 200 mg/kg of body weight of the human or animal.

7. The method according to claim 1, wherein the route of the administration is selected from the group consisting of oral, topical, suppository, intravenous, intradermic, intragaster, intramusclar, intraperitoneal, and intravenous.

8. The method according to claim 1, wherein the extract is comprised of at least 14.83% catechin/epicatechin.

9. The method according to claim 1, wherein the pain is joint pain.

10. The method according to claim 9, wherein the joint pain is osteoarthritis, rheumatoid arthritis, or systemic lupus erythematosis.

11. A method for improving joint comfort, comprising administering to a human or animal in need thereof an effective amount of an *Acacia* extract enriched for catechin and epicatechin, wherein the method alleviates cyclooxygenase and 5-lipoxygenase mediated inflammation in the human or animal.

12. The method according to claim 11, wherein the *Acacia* is selected from *Acacia catechu, Acacia concinna, Acacia farnesiana, Acacia senegal, Acacia speciosa, Acacia arabica, Acacia caesia, Acacia pennata, Acacia sinuata, Acacia mearnsii, Acacia picnantha, Acacia dealbata, Acacia auriculiformis, Acacia holoserecia,* or *Acacia mangium*.

13. The method according to claim 11, wherein the extract is from an *Acacia* plant part selected from the group consisting of stems, stem barks, trunks, trunk barks, twigs, tubers, roots, root barks, young shoots, seeds, rhizomes, flowers and other reproductive organs, leaves and other aerial parts.

14. The method according to claim 11, wherein the cyclooxygenase and 5-lipoxygenase mediated inflammation is osteoarthritis, rheumatoid arthritis, or systemic lupus erythematosis.

15. The method according to claim 11, wherein the *Acacia* extract is comprised of 0.01% to 100% of flavans.

16. The method according to claim 11, wherein the *Acacia* extract is administered at a dose of 0.01 to 200 mg/kg of body weight of the human or animal.

17. The method according to claim 11, wherein the route of the administration is selected from the group consisting of oral, topical, suppository, intravenous, intradermic, intragaster, intramusclar, intraperitoneal, and intravenous.

18. The method according to claim 11, wherein the extract is comprised of at least 14.83% catechin/epicatechin.

* * * * *